US007695426B2

(12) United States Patent
O'Neill

(10) Patent No.: US 7,695,426 B2
(45) Date of Patent: Apr. 13, 2010

(54) METHODS FOR ENHANCING VIABILITY

(75) Inventor: Christopher O'Neill, Greenwich (AU)

(73) Assignee: Biological Resources Pty Ltd (AU)

( * ) Notice: Subject to any disclaimer, the term of this patent is extended or adjusted under 35 U.S.C. 154(b) by 758 days.

(21) Appl. No.: 10/568,905

(22) PCT Filed: Aug. 20, 2004

(86) PCT No.: PCT/AU2004/001121

§ 371 (c)(1),
(2), (4) Date: Jul. 10, 2006

(87) PCT Pub. No.: WO2005/019440

PCT Pub. Date: Mar. 3, 2005

(65) Prior Publication Data

US 2007/0006332 A1     Jan. 4, 2007

(30) Foreign Application Priority Data

Aug. 20, 2003  (AU)  .............................. 2003904490

(51) Int. Cl.
*A61B 17/43*  (2006.01)
*A61D 7/00*   (2006.01)
*C12N 5/00*   (2006.01)

(52) U.S. Cl. ........................... 600/33; 600/35; 435/383; 435/384; 435/385; 435/375

(58) Field of Classification Search ................... 435/7.2, 435/375, 383, 384, 385; 600/33, 35
See application file for complete search history.

(56) References Cited

U.S. PATENT DOCUMENTS 6,593,353 B1   7/2003  Gudkov et al. .............. 514/367

FOREIGN PATENT DOCUMENTS

| EP | 0 261 798 | 3/1988 |
| WO | WO 90/13299 | 11/1990 |
| WO | WO 99/49029 | 9/1999 |
| WO | WO 01/70949 A1 | 9/2001 |

OTHER PUBLICATIONS

Komarov et al., A chemical inhibitor of p53 that protects mice from the side effects of cancer therapy, Science, vol. 285, 1999, p. 1733-1737.*
Ghosh et al., Effects of protein kinase inhibitors on the accumulation kinetics of p53 protein in normal human emcryo cells following X-irradiation, Journal of Radiation Research, vol. 40, 1999, p. 23-37.*
Hoagland, M, 2005, Pharmaceutical and Experimental Therapeutics, 314:603-610.*
Agarwal, M.L. et al., The p53 Network, *Journal of Biological Chemistry*, 1998, 273(1), 1-4.
Akimitsu, N. et al., "Induction of Apoptosis by Depletion of DNA Topoisomerase IIα in Mammalian Cells", *Biochemical and Biophysical Research Communications*, 2003, 307, 301-307.

Collins, "An International Survey of the Health Ecomomics of IVF and ICSI", *Human Reproduction Update*, 2002, 8(3), 265-277.
Emerson, M. et al., "Characterization and Functional Significance of Calcium Transients in the 2-Cell Mouse Embryo Induced by an Autocrine Growth Factor", *The Journal of Biological Chemistry*, 2000, 275(29), 21905-91913.
Hardy, K. et al., "Growth Factor Expression and Function in the Human and Mouse Preimplantation Embryo", *Journal of Endocrinology*, 2002, 172, 221-236.
Hurst, T. et al., Assisted Conception Australia and New Zealand 1999 and 2000, *Australian Institute of Health and Welfare National Perinatal Statistics Unit*, 2001, 87 pages.
Juriscova, A. et al., "Expression and Regulation of Genes Associated with Cell Death During Murine Preimplantation Embryo Development", *Molecular Reproduction and Development*, 1998, 51, 243-253.
Jurisicova, A. et al., "Deadly Decisions: The Role of Genes Regulating Programmed Cell Death in Human Preimplantation Embryo Development", *Society for Reproduction and Fertility*, 2004, 281-291.
Jurisicova, A. et al., "Programmed Cell Death and Human Embryo Fragmentation", *Molecular Human Reproduction*, 1996, 2, 93-98.
Lu, D.P. et al., "Ligand-Activated Signal Transduction in the 2-Cell Embryo", *Biology of Reproduction*, 2003, 69, 106-116.
Lu, D.P. et al., "Trophic Signals Acting Via Phosphatidylinositol-3 Kinase are Required for Normal Pre-mplantation Mouse Embryo Development", *Journal of Cell Science*, 2004, 15, 1567-1576.
Momand, J. et al., "The *mdm-2* Oncogene Product Forms a Complex with the P53 Protein and Inhibits p53-Mediated Transactivation", *Cell*, 1992, 69, 1237-1245.
O'Neill, C., "Evidence for the Requirement of Autocrine Growth Factors for Development of Mouse Preimplantation Embryos In Vitro", *Biology of Reproduction*, 1997, 56, 229-237.
O'Neill, C. et al., "Use of Bioassay for Embryo-Derived Platelet-Activating Factor as a Means of Assessing Quality and Pregnancy Potential of Human Embryos", *Fertility and Sterility*, 1987, 47(6), 969-975.
O'Neill, C. et al., "Supplementation of In-Vitro Fertilisation Culture Medium with Platelet Activating Factor", *The Lancet ii*, 1989, 769-772.
Ogawara, Y. et al., "Akt Enhances Mdm2-Mediated Ubiquitination and Degradation of p53", *Journal of Biological Chemistry*, 2002, 277(24), 21843-21850.
Poste, G. et al., "Lipid Vesicles as Carriers for Introducing Biologically Active Materials into Cells", *Methods in Cell Biology*, 1976, vol. 14, 33-71.

(Continued)

*Primary Examiner*—Valarie Bertoglio
(74) *Attorney, Agent, or Firm*—Fenwick & West LLP

(57) ABSTRACT

Methods are provided for enhancing viability comprising administering at least one inhibitor of p53 or a p53-associated pathway to one or more of the following: the embryo, oocytes, sperm, a femme animal or a male animal.

23 Claims, 9 Drawing Sheets

OTHER PUBLICATIONS

Ryan, J.P. et al., "Implantation Potential and Fetal Viability of Mouse Embryos Cultured in Media Supplemented with Platelet-Activating Factor", *Journal of Reproduction and Fertility*, 1990, 89, 309-315.

Sherr, C.J., "Principles of Tumor Suppression", *Cell*, 2004, 116, 235-246.

Stojanov, T. et al., "In Vitro Fertilization Causes Epigenetic Modifications to the Onset of Gene Expression from the Zygotic Genome in Mice", *Biology and Reproduction*, 2001, 64, 696-705.

Stojanov, T. et al., In-Vitro Fertilization and Culture of Mouse Embryos in vitro Significantly Retards the Onset of Insulin-Like Growth Factor-II Expression from the Zygotic Genome, *Molecular Human Reproduction*, 1999, 5(2),116-124.

Lieber, A and Strauss, M. et al., "Selection of Efficient Cleavage Sites in Target RNAs by Using a Ribozyme Expression Library", *Molecular and Cellular Biology*, 1995, 15, 540-551.

* cited by examiner

A

B

A

B

C

METHODS FOR ENHANCING VIABILITY

CROSS-REFERENCE TO RELATED APPLICATIONS

This application is the National Stage of International Application No. PCT/AU2004/001121, filed Aug. 20, 2004, which claims priority to Australian Patent Application No. 2003904490, filed Aug. 20, 2003, both of which are incorporated by reference herein in their entirety.

TECHNICAL FIELD

The present invention relates generally to methods and compositions for enhancing the viability of embryos, in particular embryos produced by assisted reproductive technologies. The present invention further relates to methods of protecting embryos from positive selection pressure for inherited defects.

BACKGROUND OF THE INVENTION

Failure of survival of the embryo over the first weeks of its existence is considered to be a major cause of subfertility and infertility in mammals. This is particularly exemplified by embryos produced by assisted reproductive technologies (ART), including in vitro fertilisation (IVF) and all related techniques. A large proportion of ART embryos are lost during the pre- and immediate post-implantation periods through apoptosis.

A total of 27,067 ART treatment cycles were performed in Australia in 2000 (Hurst and Lancaster, 2001, *AIHW National Perinatal Statistics Unit, Sydney*, ISSN 10387234) resulting in 4,319 viable pregnancies (success rate of 16%). Given that an average of 2.1 embryos were transferred per treatment cycle (and over 90% of successful treatment cycles had 2 or more embryos transferred), this equates to less than 10% of embryos produced by ART having the capacity for long-term viability. ART is expensive. The average cost per treatment cycle in the USA is US$9547 (Collins, 2002, *Human Reproduction Update.* 8:265-77).

It is well established that much of the loss of embryo viability during ART occurs in the preimplantation phase or soon after implantation. ART causes a characteristic retardation of embryo development so that 96-120 h after fertilization embryos are commonly at least a full day behind their naturally produced counterparts in their developmental program. There are also fewer cells per embryo and many of the cells in embryos undergo apoptosis (Jurisicova et al., 1996, *Molecular Human Reproduction.* 2:93-8; O'Neill, 1997, *Biology of Reproduction.* 56, 229-237). In many cases the phenotype is sufficiently severe to result in the degeneration of the entire embryo. This retardation is a consequence of cellular stressors related to culture conditions. The preimplantation embryo constitutively expresses the machinery necessary for apoptosis and possesses the effectors and regulatory elements of apoptosis. Successful embryo development seems to require the suppression of this apoptotic machinery. Attempts at treatment of the various stressors have met with only limited success. For example, an interaction between oxidative damage and reduced stimulation of embryos by autocrine and paracrine growth/survival factors is a significant contributor to IVF-induced embryonic death. However relief from oxidative stress and provision of a wide range of putative embryonic survival/growth factors only partially ameliorate the effect of IVF. This suggests that there are other relevant stressors acting on the embryo, and/or that the nature of action of stressors on the embryo is not yet well defined.

Loss of embryo viability is a significant factor limiting the success of ART and there is a clear need to more completely elucidate the factors which lead to reduced embryo death during ART and to devise appropriate strategies to improve ART embryo viability.

Much is known about the response of somatic cells to various environmental stresses. For example, cells respond to many forms of genotoxic and nongenotoxic stress by the stabilisation and increased expression of the transcription factor p53 (see for example Agarwal et al., 1998, *Journal of Biological Chemistry* 273, 1-4). p53 is a 'sensor' of cell stress that plays an important role in maintaining normal genome stability. p53 operates within a complex network of interconnected cellular pathways by which cells sense and respond to inappropriate stresses. Other tumour suppressors operating within this network include, but are not limited to, Rb, PTEN, p21, p27, ARF and INK.

p53 has the capacity to either induce reduced cycle-cell progression (by the induction of CDK inhibitors such as p21) or to induce apoptosis (by inducing the synthesis of pro-apoptotic mediators such as Bax, PUMA, AIF, etc). Mutations in p53 lead to loss of regulation of cellular processes and are associated with the development of many cancers. Mutations in p53 are found in more than half of all human cancers. It is also now believed that many adult diseases derive, at least in part, from constraints during embryonic and fetal development, including during the embryo pre-implantation stage. Accordingly, an understanding of the stresses acting on the embryo and the embryo's response to these strategies will be important in devising strategies to minimise the onset of many adult diseases.

Preimplantation mammalian embryos normally produce an array of trophic factors that act to stimulate growth and survival of the embryo (Hardy and Spanos (2002) *Journal of Endocrinology* 172, 221-236). A major cause of the reduced viability of embryos produced by ART is diminished production of a number of these growth factors. For example, it has been observed that the production of platelet activating factor (PAF; 1-0-alkyl-2-acetyl-sn-glyceryl-3-phoshocoline) and insulin-like growth factor II (IGF-II) is retarded in IVF-derived embryos (O'Neill et al., 1987, *Fertility and Sterility* 47, 969-975; and Stojanov et al., 1999, *Molecular Human Reproduction* 5, 116-124).

Such observations have led to the development of a range of protocols for the supplementation of in vitro embryo culture media with exogenous trophic factors, including PAF (Ryan et al., 1990, *Journal of Reproduction and Fertility* 89, 309-315; O'Neill et al., 1989, *The Lancet* ii, 769-772), in an effort to increase embryo viability. However the efficacy of such media supplementation is limited. Australian Patent No. 608530 describes the use of exogenous PAF or PAF analogue to increase the rate of implantation. However the effect observed was not a great as had been anticipated. Given the experimental evidence of the requirement for autocrine and paracrine trophic factors in normal embryonic development (O'Neill, 1997, *Biology of Reproduction* 56, 229-237), this clinical outcome is surprising.

Accordingly, there is a need for improved methods for enhancing embryo viability.

SUMMARY OF THE INVENTION

According to a first aspect of the present invention there is provided a method for enhancing embryo viability, the method comprising administering at least one inhibitor of p53 or a p53-associated pathway to one or more of the following: the embryo, oocytes, sperm, a female animal or a male animal.

The inhibitor may be an inhibitor of one or more of the following: p53, Rb, PTEN, p21, p27, ARF and INK. In one embodiment the inhibitor is a p53 inhibitor. The inhibitor may be selected from the group consisting of: a small molecule inhibitor, a nucleic-acid based inhibitor, a peptide-based inhibitor and any combination thereof.

The at least one inhibitor may be added as a supplement to a culture medium containing the embryo and/or gametes.

Two or more inhibitors of p53 or a p53-associated pathway may be administered. The two or more inhibitors may be inhibitors of the same or different molecules. The molecules may be selected from the group consisting of: p53, Rb, PTEN, p21, p27, ARF and INK.

According to a second aspect of the present invention there is provided a method for enhancing embryo viability, the method comprising administering at least one p53 inhibitor to one or more of the following: the embryo, oocytes, sperm, a female animal or a male animal.

The p53 inhibitor may be selected from the group consisting of: a small molecule inhibitor, a nucleic-acid based inhibitor, a peptide-based inhibitor and any combination thereof. The inhibitor may be a small molecule inhibitor such as pifithrin-α (PFT-α) or a derivative or analogue thereof. The inhibitor may be a p53-specific antisense molecule such as a p53-specific siRNA.

In an embodiment two or more p53 inhibitors may be administered. The two or more inhibitors may be a small molecule inhibitor and a p53-specific siRNA.

According to a third aspect of the present invention there is provided a method for enhancing embryo viability, the method comprising administering at least one inhibitor of p53 or a p53-associated pathway and at least one growth promoting agent to one or more of the following: the embryo, oocytes, sperm, a female animal or a male animal.

The growth promoting agent may be a trophic factor or analogue or derivative thereof, or an agent capable of activating a trophic factor-associated signalling pathway. This may be achieved by transient exposure of embryos to calcium ionophores, such as ionomycin.

The trophic factor may be selected from the group consisting of: platelet activating factor (PAF), insulin-like growth factors-I (IGF-I) and -II (IGF-II), transforming growth factor-α (TGF-α), epidermal growth factor (EGF), leukemia inhibitory factor (LIF), colony stimulating factor-I (CSF-I), and granulocyte-macrophage colony stimulating factor (GM-CSF).

In one embodiment the trophic factor is PAF or an analogue or derivative thereof.

In one embodiment the trophic factor is IGF-II or an analogue or derivative thereof.

The inhibitor may be an inhibitor of one or more of the following: p53, Rb, PTEN, p21, p27, ARF and INK.

According to a fourth aspect of the present invention there is provided a method for enhancing embryo viability, the method comprising administering at least one p53 inhibitor and at least one growth promoting agent to one or more of the following: the embryo, oocytes, sperm, a female animal or a male animal.

In one embodiment, the at least one p53 inhibitor is PFT-α and the at least one growth promoting agent is PAF.

In one embodiment, the at least one p53 inhibitor is PFT-α and the at least one growth promoting agent is IGF-II.

In one embodiment, the at least one p53 inhibitor is a p53-specific siRNA and the at least one growth promoting agent is PAF.

In one embodiment, the at least one p53 inhibitor is a p53-specific siRNA and the at least one growth promoting agent is IGF-II.

According to a fifth aspect of the present invention there is provided a composition for enhancing embryo viability, the composition comprising at least one inhibitor of p53 or a p53-associated pathway, together with one or more pharmaceutically acceptable carriers.

According to a sixth aspect of the present invention there is provided a composition for enhancing embryo viability, the composition comprising at least one p53 inhibitor, together with one or more pharmaceutically acceptable carriers.

According to a seventh aspect of the present invention there is provided a composition for enhancing embryo viability, the composition comprising at least one inhibitor of p53 or a p53-associated pathway and at least one growth promoting agent, together with one or more pharmaceutically acceptable carriers.

According to an eighth aspect of the present invention there is provided a composition for enhancing embryo viability, the composition comprising at least one p53 inhibitor and at least one growth promoting agent, together with one or more pharmaceutically acceptable carriers.

The compositions according to the fifth to the eighth aspect may be administered to one or more of the following: the embryo, oocytes, sperm, a female animal or a male animal.

According to a ninth aspect of the present invention there is provided a method for enhancing embryo viability, the method comprising administering to one or more of the embryo, oocytes, sperm, a female animal or a male animal an effective amount of a composition according to any one of the fifth to the eighth aspects.

According to a tenth aspect of the present invention there is provided a method of in vitro fertilisation of oocytes, the method comprising the steps of:

(a) recovering at least one oocyte from a female animal;

(b) incubating in vitro the oocyte with sperm to produce at least one embryo; and (c) culturing the embryo in a suitable embryo growth medium, wherein at least one of the female animal, the recovered oocyte(s), the sperm, the male animal from which the sperm are isolated and/or the cultured embryo are treated with an effective amount of at least one inhibitor of p53 or a p53-associated pathway.

According to an eleventh aspect of the present invention there is provided a method of in vitro fertilisation of oocytes, the method comprising the steps of:

(a) recovering at least one oocyte from a female animal;

(b) incubating in vitro the oocyte with sperm to produce at least one embryo; and (c) culturing the embryo in a suitable embryo growth medium, wherein at least one of the female animal, the recovered oocyte(s), the sperm, the male animal from which the sperm are isolated and/or the cultured embryo are treated with an effective amount of at least one inhibitor of p53 or a p53-associated pathway and at least one growth promoting agent.

The method of the tenth or eleventh aspect may further comprise the step of:

(d) transferring the embryo to the reproductive tract of the female animal.

According to a twelfth aspect of the present invention there is provided a composition for use as an in vitro gamete or embryo growth medium, the composition comprising an effective amount of at least one inhibitor of p53 or a p53-associated pathway together with one or more suitable salts and/or nutrients.

According to a thirteenth aspect of the present invention there is provided a composition for use as an in vitro gamete or embryo growth medium, the composition comprising an effective amount of at least one inhibitor of p53 or a p53-associated pathway and at least one growth promoting agent together with one or more suitable salts and/or nutrients.

According to a fourteenth aspect of the present invention there is provided a method of preventing apoptosis in an embryo, the method comprising administering at least one inhibitor of p53 or a p53-associated pathway to one or more of the following: the embryo, oocytes, sperm, a female animal, or a male animal.

The method may further comprise administering an effective amount of at least one growth promoting agent.

According to a fifteenth aspect of the present invention there is provided a method of increasing pregnancy rates resulting from assisted reproductive technologies, wherein the method comprises temporarily inhibiting the expression or activity of p53 or a p53-associated pathway.

Temporary inhibition of expression or activity may be achieved by the administration of an effective amount at least one inhibitor of p53 or a p53-associated pathway to one or more of the following: in vitro-cultured embryos, isolated oocytes, sperm, a female animal or a male animal.

According to a sixteenth aspect of the present invention there is provided a method of increasing the pregnancy rate of a female animal undergoing in vitro fertilisation, the method comprising the steps of:

(a) recovering at least one oocyte from the female animal;

(b) incubating in vitro the oocyte with sperm to produce at least one embryo;

(c) culturing the embryo in a suitable embryo growth medium; and (d) transferring the embryo to the reproductive tract of the female animal, wherein at least one of the female animal, the recovered oocytes, the sperm, the male animal from which the sperm are isolated and/or the cultured embryo are treated with an effective amount of at least one inhibitor of p53 or a p53-associated pathway.

The method may further comprise administering an effective amount of at least one growth promoting agent.

According to a seventeenth aspect of the present invention there is provided a method for increasing the ovulation rate in a female animal; the method comprising administering to the female animal an effective amount of at least one inhibitor of p53 or a p53-associated pathway.

The method may further comprise administering an effective amount of at least one growth promoting agent and/or an ovulation inducing agent.

According to an eighteenth aspect of the present invention there is provided a method for increasing the fertilising capacity of sperm, the method comprising administering to a male animal or isolated sperm an effective amount of at least one inhibitor of p53 or a p53-associated pathway.

The method may further comprise administering an effective amount of at least one growth promoting agent.

According to a nineteenth aspect of the present invention there is provided a process for identifying an agent for enhancing embryo viability, the process comprising contacting a cell, cell extract or embryo with a candidate agent, determining whether the agent causes temporary inhibition of the expression or activity of p53 or a component of a p53-associated pathway, and thereby determining whether the agent is capable of enhancing embryo viability.

According to a twentieth aspect of the present invention there is provided a method for enhancing embryo viability, the method comprising administering an effective amount of at least one agent identified by the process of the nineteenth aspect to one or more of the following: the embryo, oocytes, sperm, a female animal or a male animal.

According to a twenty first aspect of the present invention there is provided a method of protecting an embryo from positive selection pressure for inherited or acquired defects, the method comprising administering at least one inhibitor of p53 or a p53-associated pathway to one or more of the following: the embryo, oocytes, sperm, a female animal or a male animal.

According to a twenty second aspect of the present invention there is provided a method of preventing or reducing the accumulation of loss-of-function mutations in p53 in a developing embryo, the method comprising administering at least one inhibitor of p53 or a p53-associated pathway to one or more of the following: the embryo, oocytes, sperm, a female animal or a male animal.

According to the tenth to the twenty second aspects the inhibitor may be a p53 inhibitor.

According to the above aspects and embodiments of the present invention, typically the female animal is a mammal selected from the group consisting of: primate, ovine, bovine, canine, feline, porcine, equine or murine. According to specific embodiments the female animal is a human or a bovine. Similarly, typically the sperm, oocytes and embryos are mammalian embryos selected from the group consisting of: primate, ovine, bovine, canine, feline, porcine, equine or murine. In particular embodiments the sperm, oocytes and embryos are human sperm, oocytes and embryos or bovine sperm, oocytes and embryos.

DEFINITIONS

In the context of this specification, the term "comprising" means "including principally, but not necessarily solely". Furthermore, variations of the word "comprising", such as "comprise" and "comprises", have correspondingly varied meanings.

In the context of this specification "p53-associated pathway" means any cellular pathway forming part of the interconnected network of pathways involving p53. Such pathways may operate, downstream of p53, upstream of p53 or may otherwise operate prior to, in conjunction with, or as a consequence of p53 activity, and thus include components or members that may interact directly with p53, interact indirectly with p53 or otherwise operate downstream of p53, upstream of p53 or may otherwise operate prior to, in conjunction with, or as a consequence of p53 activity. Reference herein to a p53-associated pathway therefore includes reference to the members or components of the pathway.

In the context of this specification, the term "inhibitor of p53 or a p53-associated pathway" refers to any agent or action capable of inhibiting the expression or activity of p53 or a component of a p53-associated pathway. Accordingly the inhibitor may operate directly or indirectly on p53 or the p53 gene, or alternatively act via the direct or indirect inhibition of any one or more components of a p53-associated pathway. Such components may be molecules activated, inhibited or otherwise modulated prior to, in conjunction with, or as a consequence of p53 activity. Thus, the inhibitor may operate to prevent transcription, translation, post-transcriptional or post-translational processing or otherwise inhibit the activity of p53 or a component of a p53-associated pathway in any way, via either direct or indirect action. The inhibitor may for example be nucleic acid, peptide, any other suitable chemical compound or molecule or any combination of these. Additionally, it will be understood that in indirectly impairing the activity of p53 or a component of a p53-associated pathway, the inhibitor may effect the activity of other cellular molecules which may in turn act as regulators of the molecule itself. Similarly, the inhibitor may affect the activity of molecules which are themselves subject to regulation or modulation by p53 or a component of a p53-associated pathway.

In the context of this specification, the term "specific" as it pertains to a nucleic-acid based inhibitor, such as a p53-specific antisense molecule, means substantially specific, but not necessarily exclusively so. The inhibitor should display sufficient specificity for the gene in question to temporarily inhibit the expression or activity of the gene. For example, the nucleotide sequence of an antisense molecule according to the present invention may display less than 100% sequence identity with a p53-encoding polynucleotide, and may cross-hybridize with other sequence, while retaining specificity for p53.

In the context of this specification, the term "activity" as it pertains to p53 or a component of a p53-associated pathway means any cellular function, action, effect or influence exerted by p53 or the component, either by a nucleic acid sequence or fragment thereof encoding the product, or by the gene product itself or any fragment thereof. "Activity" may therefore relate to the activity of p53 component of a p53-associated pathway on a gene or gene product acting downstream thereof and the term "activity" is therefore interpreted as also encompassing the p53 or associated pathway-dependent expression and activities of these downstream genes and gene products.

The term "expression" as used herein refers interchangeably to expression of a gene or gene product, including the encoded protein. Expression of a gene may be determined, for example, by measuring the production of messenger RNA (mRNA) transcript levels. Expression of a polypeptide gene product may be determined, for example, by immunoassay using an antibody(ies) that bind with the polypeptide.

The term "fragment" as used herein refers to a nucleic acid or polypeptide sequence that encodes a constituent or is a constituent of a full-length gene or protein and possesses qualitative biological activity in common with the full-length molecule.

In the context of this specification, the terms "enhancing the viability of an embryo" and "enhancing embryo viability" mean enhancing or increasing the likelihood of survival of an embryo(s) which has been treated with or exposed to, either directly or indirectly, agents or compositions according to the invention compared to the likelihood of survival of an embryo(s) which has not been treated with or exposed to, either directly or indirectly, such agents or compositions.

In the context of this specification, the term "an effective amount" includes within its meaning a non-toxic but sufficient amount of an agent or inhibitor to provide the desired effect. The exact amount required will vary from subject to subject depending on factors such as the species being treated, the age and general condition of the subject, the particular agent or inhibitor being administered and the mode of administration and so forth. Thus, it is not possible to specify an exact "effective amount". However, for any given case, an appropriate "effective amount" may be determined by one of ordinary skill in the art using only routine experimentation.

In the context of this specification, the term "temporary inhibition" means that inhibition is not permanent but rather is short term and reversible. That is, activity or expression of the gene or gene product is not permanently inactivated, but rather expression or activity is inhibited for a time sufficient to produce the desired effect and when the effects of the inhibitor have diminished or ceased, the molecule is available to carry out its normal cellular functions.

In the context of this specification, the term "growth-promoting agent" means a trophic factor, analogue or derivative thereof or a compound capable of activating or stimulating a trophic factor-associated signalling pathway. The term "trophic factor" refers to a growth factor capable of stimulating or promoting the growth and/or development and/or survival of an embryo or stimulates increased activity in the embryo. The trophic factor may be an autocrine, paracrine or endocrine trophic factor. That is, the trophic factor may be one that is normally produced by the embryo itself or is normally maternally-derived.

BRIEF DESCRIPTION OF THE DRAWINGS

The present invention will now be described by way of example with reference to the accompanying drawings.

BEST MODE OF PERFORMING THE INVENTION

Figure 1:
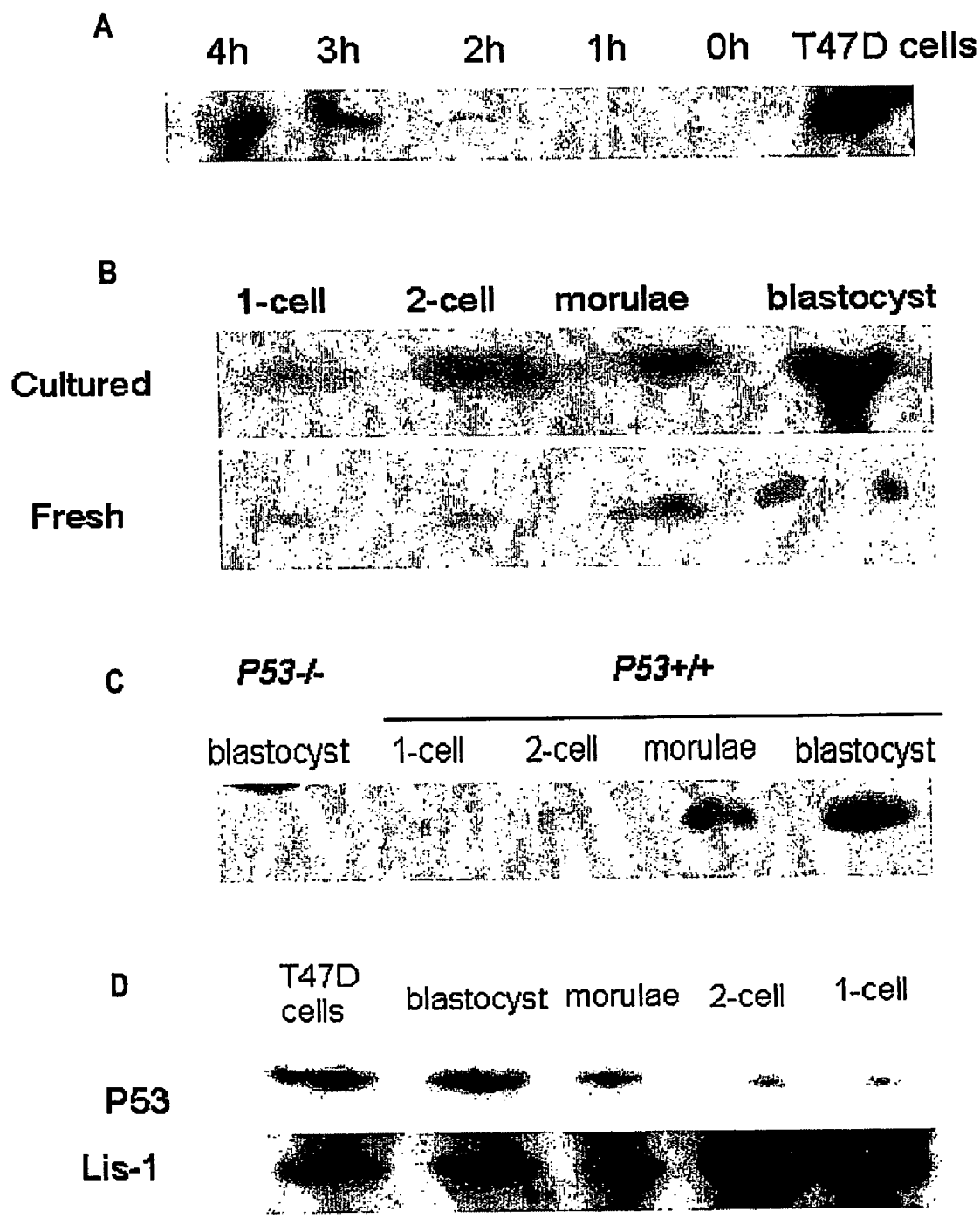
FIG. 1. Western blot analysis of p53 expression. (A) Production of p53 by sperm after dilution into capacitation media. (B) Expression of p53 in p53$^{+/+}$ mouse embryos cultured from the zygote stage until the developmental stage indicated or collected fresh from the reproductive tract at the developmental stage indicated. Each blot shows the p53 expressed by the equivalent of 30 embryos. (C) Specificity of the western blot assay. (D) A comparison of p53 and Lis-1 expression at various embryo developmental stages and in T47D cells.

The p53 gene is known to play a crucial role as a tumour suppressor gene—it is estimated that loss of function mutations in p53 are found in more than half of all human cancers. Other functions of p53 and similar tumour suppressors in normal cells and tissues are also increasingly being identified, for example as cell cycle checkpoint regulators (Sherr, 2004, Cell 116, 235-246). Accordingly, the inactivation of p53 has generally been viewed as undesirable.

p53 forms part of an interconnected network of pathways that allow cells to sense and respond to inappropriate stresses. Examples of tumour suppressors acting in p53-associated pathways include but are not limited to Rb, PTEN, P21, P27 ARF and INK.

The present invention is predicated, in part, on the inventor's surprising finding that expression of p53 is upregulated in embryos produced by assisted reproductive technologies (ART) such as in vitro fertilisation (IVF) and that this upregulation correlates with poor embryo viability following ART. Recognising that permanent inhibition of p53 in the developing embryo is undesirable, the inventor demonstrates herein that short term inhibition of p53 during the culture of gametes or embryos in vitro can increase the viability of embryos. For example, the proportion of embryos developing into morphologically normal blastocysts can be increased, the number of cells per blastocyst increased and the number of cells in the embryo undergoing apoptosis decreased.

In one aspect, the present invention provides a method of enhancing embryo viability by administering to one or more of the embryo, oocytes, a female animal, sperm and a male animal an effective amount of at least one inhibitor of p53 or a p53-associated pathway. The inhibitor may be an inhibitor of one or more of the following: p53, Rb, PTEN, P21, P27 ARF and INK. More than one inhibitor or one or more of the above may be administered according to methods of the invention.

A large number of trophic factors have also been shown to have effects on the growth, development and survival of pre-implantation mammalian embryos, many of which are produced by the embryo itself (reviewed in Hardy and Spanos (2002) Journal of Endocrinology 172, 221-236). These include, but are not limited to, platelet activating factor (PAF), insulin-like growth factors-I (IGF-I) and -II (IGF-II), transforming growth factor-α (TGF-α), epidermal growth factor (EGF), leukemia inhibitory factor (LIF), colony stimulating factor-I (CSF-I), and granulocyte-macrophage colony stimulating factor (GM-CSF).

Studies have demonstrated that ART embryos are deficient in several trophic factors but that provision of these factors exogenously has only a small beneficial effect in terms of restoring normal trophic factor functioning and increasing implantation rates and/or embryo viability. As described herein, studying PAF as an example, the present inventor has found that poor response of ART embryos to exogenous trophic factor addition is due to a reduced capacity of embryos cultured in vitro to respond to trophic stimulation. This reduced capacity to respond is manifested as both a reduced amplitude of response and a decrease in the proportion of embryos that respond.

There is good evidence that the mechanism by which embryonic trophic factors exert their effects on the embryo are highly redundant of each other (Lu et al. (2003) *Journal of Cell Science* 15, 1567-1576), involving among other mechanisms the phosphosphatidylinositol-3-kinase pathway, and further that the actions of several trophic factors are similar, but not apparently additive. It can therefore be reasonably argued and those skilled in the art would readily appreciate that the deficiencies observed in ART embryos in relation to exogenous PAF administration also occur for many of the embryonic trophic factors, including IGF-I, IGF-II, TGF-α, EGF, LIF, CSF-I and GM-CSF.

As disclosed herein, the inventor has now demonstrated that the upregulation of p53 observed in embryos resulting from ART contributes to the limited benefit achieved by the addition of exogenous trophic factors to embryos in vitro. Treatment of in vitro cultured embryos with both an inhibitor of p53 and a trophic factor leads to a significantly greater increase in embryo viability than treatment of embryos with either the trophic factor alone or a p53 inhibitor alone.

Accordingly, in a further aspect, the present invention provides a method of enhancing embryo viability by administering to one or more of the embryo, oocytes, a female animal sperm and a male animal an effective amount of at least one inhibitor of p53 or a p53-associated pathway and at least one growth promoting agent. In particular embodiments the growth promoting agent is a trophic factor, such as PAF, an analogue or derivative thereof or IGF-II, an analogue or derivative thereof.

p53 forms part of an interconnected network of pathways that allow cells, including gametes, and the embryo to sense and respond to inappropriate stresses. As disclosed herein, embodiments of the present invention demonstrate that disruption of key components of this network has the capacity to enhance the viability of gametes and embryos. While the disclosure following focuses largely on the inhibition of p53, those skilled in the art will readily appreciate that other components of p53-associated pathways, including for example, Rb, PTEN, P21, P27 ARF and INK may also be inhibited to achieve the desired effect. Accordingly, embodiments of methods and compositions of the present invention contemplate the use of inhibitors or p53 and p53-associated pathways.

For the purposes of the present invention, embryo viability may be reflected in a number of indicators. For example increased embryo viability may result in increased embryo implantation rates following in vitro fertilisation, decreased pre- and post-implantation embryo lethality, increased clinical pregnancy rates or increased birth rates. The present invention therefore also relates to methods of preventing apoptosis or retarded development in embryos and to methods of increasing pregnancy rates in animals.

The present invention is of particular benefit in increasing embryo viability following ART, and in particular IVF. Other suitable ART techniques to which the present invention is applicable include, but are not limited to, gamete intrafallopian transfer (GIFT), zygote intrafallopian transfer (ZIFT), blastocyst transfer (BT), intracytoplasmic sperm injection (ICSI), gamete, embryo and cell cryopreservation, in vitro preparation of embryos such as in vitro oocyte maturation, embryo biopsy and other forms of embryo micromanipulation including formation of embryos by nuclear transfer and production transgenic lines and genetically modified lines. It is also applicable to production of embryonic stem cell lines.

Those of skill in the art will appreciate that the advantages offered by the present invention are not limited to ART-generated embryos. Rather the methods and compositions of the present invention are equally applicable as treatment to improve the viability of all embryos, whether they are produced in vitro via ART or in the reproductive tract of the animal. The methods of the present invention are therefore also applicable to improving embryo viability and pregnancy rates in otherwise unassisted pregnancies. Embodiments of the present invention also provide for methods of increasing ovulation rates in female animals and methods of increasing the fertilizing capacity of sperm in male animals.

The methods and compositions of the present invention are of use not only for human reproduction, but for a variety of species. For example, the methods and compositions of the present invention can be used to improve embryo viability and pregnancy rates in animal husbandry, for species of agricultural value, and in species bred for conservation purposes. In particular the present invention finds application in vertebrates, and more particularly in mammals. For example, as disclosed herein, embodiments of the methods and compositions of the invention find application in bovine reproduction.

Further, the methods and compositions of the present invention are not only applicable to improving embryo viability for the purposes of increasing the success rate of a pregnancy, but find application in all circumstances in which it is beneficial to improve embryo viability, for example in the production of embryonic stem cells, the production of cloned embryos, the formation of embryonic chimera, the production of transgenic or genetically modified cell lines and organisms, cryopreservation and all related techniques.

To achieve the desired result, agents and inhibitors according to embodiments of the invention may be administered directly to an embryo, for example as a supplement to the medium in which the embryo is being cultured in vitro. Alternatively, either, or both, of the male gametes or the female gametes may be treated prior to fertilisation. Further, the present invention also contemplates the treatment of a female animal or a male animal directly with a composition of the invention.

Also disclosed herein are processes for the screening and identification of agents for to increasing embryo viability, the processes comprising contacting a cell, cell extract or embryo with a candidate agent, determining whether the agent causes temporary inhibition of the expression or activity of p53 or a component of a p53-associated pathway, and thereby determining whether the agent is capable of increasing embryo viability. Typically the candidate agents are compounds that are not previously known to inhibit the expression or activity of the molecule in question. The cell is may be, for example, a sperm cell, an oocyte or an embryonic stem cell.

Inhibition of p53 and p53-Associated Pathways

According to embodiments of the present invention, the inhibition of p53 or a p53-associated pathway suitable to achieve the desired outcomes is temporary inhibition. That is, inhibition is short term and reversible. For example, permanent inhibition of p53 is undesirable due to the importance of p53 activities. However as disclosed herein the short term inhibition of p53 during the culture of embryos in vitro can increase the viability of embryos. For example the proportion of embryos developing into morphologically normal blastocysts can be increased, the number of cells per blastocyst increased and the number of cells in the embryo undergoing apoptosis decreased.

For embryos and gametes in in vitro culture, treatment with at least one suitable inhibitor is preferably for the duration of the in vitro culture period of the embryos or gametes, or for a portion of this time. The appropriate duration of exposure to a suitable inhibitor can be readily determined by those skilled in the art by routine experimentation.

For embryos produced by ART, at least one inhibitor may be added as a supplement to the media in which the embryo is cultured, or in which gametes are cultured. Alternatively or in addition the female animal from which the oocytes are recovered and/or the male animal from which the sperm are collected may be treated with at least one inhibitor. It will be appreciated that any suitable concentration of inhibitor may be used, and the appropriate concentration will likely depend on a number of factors including but not limited to the nature, mode of action and toxicity of the inhibitor and the species of animal concerned. That is, for example, the optimal concentration of inhibitor, and optimal time and mode of delivery may vary between species. One skilled in the art would be able to determine, by routine experimentation, the appropriate parameters for use in any given circumstance.

In all instances the appropriate concentration is one that is sufficient to reduce or prevent the adverse effects of p53 or a component of a p53-associated pathway on embryo survival. By way of example, the inhibitor may be administered in a concentration of between about 0.01 µM and about 50 µM, between about 0.1 µM and about 20 µM, between about 0.5 µM and about 15 µM, between about 1 µM and about 10 µM, or between about 2 µM and about 10 µM. The exact concentration suitable for use in the methods of the invention will depend on a number of factors including, for example, the subject of the administration (i.e. embryo, isolated cells or individual), the species to be treated, the mode of administration and the inhibitor to be administered. One skilled in the art would be able to determine, by routine experimentation, the appropriate concentration to be used in any given circumstance.

The description of suitable inhibitors below is provided with particular reference to inhibitors of p53. However this description should not be construed as in any way limiting the invention thereto. Rather those skilled in the art will readily appreciate that p53-associated pathways and components or members of these pathways may also be inhibited using similar mechanisms to achieve the desired effect, and such inhibition is within the scope of the present invention.

Inhibition of p53

A p53 inhibitor suitable for use in the methods of the present invention is one that provides reversible inhibition, provides inhibition for a time sufficient to prevent p53-induced loss of viability in the developing embryo and that has low toxicity. A p53 inhibitor suitable for use according to the present invention may be a small molecule inhibitor, a nucleic-acid based inhibitor, a peptide-based inhibitor or any combination thereof.

Such an inhibitor may act directly or indirectly on p53. For example the inhibitor may act to impair or prevent nuclear import and/or export of p53, may decrease the stability of p53 or may block any one or more of a number of other actions thereof, such as transcriptional activation of downstream acting genes. For example, p53 activates transcription of a number of genes encoding pro-apoptotic and cell-cycle arrest mediators, including, for example, bax, p21/waf1, IGF-BP3 and PUMA (Agarwal et al., 1998, *Journal of Biological Chemistry* 273, 1-4). The present invention relates to the prevention of apoptosis or cell arrest in embryos which is initiated by p53, and accordingly, contemplates the inhibition of transcription or functioning of apoptosis- or arrest-inducing factors regulated by p53 such as those referred to above.

Additionally a suitable inhibitor may exert its inhibitory effect on p53 activity via its interaction with or effect on a regulator of p53. For example, a key regulator of p53 activity is MDM-2 (Momand et al., 1992, *Cell*. 69:1237-45). MDM-2 causes nuclear export, ubiquination and degradation of p53 hence limiting its actions. A canonical regulator of MDM-2 activity is its phosphorylation by the PI3K/Akt signalling pathway (Ogawara et al, 2002, *Journal of Biological Chemistry*. 277:21843-50).

In one embodiment of the invention the p53 inhibitor is a small molecule inhibitor. One particularly suitable small molecule inhibitor for use in the methods of the invention is pifithrin-α (PFT-α; 2-(2-imino-4,5,6,7-tetrahydrobenzothiazol-3-yl)-1-p-tolylethanone) (Komarov et al., 1999, *Science*. 285:1733-1737) or variant or analogue thereof. The present inventor has demonstrated that the addition of between 0.1 and 20 μM of PFT-α to embryos in culture has a significant effect on increasing embryo survival.

It will be appreciated by those skilled in the art that temporary inhibition is achievable by a variety of means other than use of a chemical inhibitor such as PFT-α. For example, nucleic acid-based and peptide-based inhibitors are also contemplated, and a number of alternative approaches to achieving temporary p53 inhibition may be used in the methods of the present invention.

For example embodiments of the invention may utilise antisense technology to inhibit the expression of a p53 gene by blocking translation of the protein. Antisense technology takes advantage of the fact that nucleic acids pair with complementary sequences. Suitable p53-specific antisense molecules can be manufactured by chemical synthesis or, in the case of antisense RNA, by transcription in vitro or in vivo when linked to a promoter, by methods known to those skilled in the art. A number of factors may operate to vary the level of inhibition achieved using an antisense construct according to the present invention, including, for example, the design of the construct (nucleotide sequence), dose of the construct used, dose of any transfection agent used and whether gametes, oocytes or individuals are treated.

For example, antisense oligonucleotides, typically of 18-30 nucleotides in length, may be generated which are at least substantially complementary across their length to a region of the nucleotide sequence of the p53 gene. Binding of the antisense oligonucleotide to their complementary cellular nucleotide sequences may interfere with transcription, RNA processing, transport, translation and/or mRNA stability. Suitable antisense oligonucleotides may be prepared by methods well known to those of skill in the art and may be designed to target and bind to regulatory regions of the nucleotide sequence or to coding (exon) or non-coding (intron) sequences. Typically antisense oligonucleotides will be synthesized on automated synthesizers. Suitable antisense oligonucleotides may include modifications designed to improve their delivery into cells, their stability once inside a cell, and/or their binding to the appropriate target. For example, the antisense oligonucleotide may be modified by the addition of one or more phosphorothioate linkages, or the inclusion of one or morpholine rings into the backbone (so-called 'morpholino' oligonucleotides).

By way of example only, a p53-specific antisense molecule may be administered in a concentration of between about 0.01 nM and about 200 nM, between about 0.1 nM and about 100 nM, between about 0.5 nM and about 50 nM, between about 1 nM and about 25 nM, or between about 2 nM and about 20 nM. However those skilled in the art will readily appreciate that for any given antisense molecule the exact concentration to be used in any given circumstance should be determined empirically and will depend on a number of factors including, for example, the molecule to be administered, the method of transfection, the transfection agent(s) used, if any, the subject of the treatment (i.e. embryo, isolated cells, an individual) and the species to be treated. One skilled in the art would be able to determine, by routine experimentation, the appropriate concentration to be used in any given circumstance.

One suitable antisense technology, known as RNA interference (RNAi), may be used, according to known methods in the art (for example WO 99/49029 and WO 01/70949, the disclosures of which are incorporated herein by reference), to inhibit the expression of p53 according to methods and compositions of the invention. RNAi refers to a means of selective post-transcriptional gene silencing by destruction of specific mRNA by small interfering RNA molecules (siRNA). The siRNA is generated by cleavage of double stranded RNA, where one strand is identical to the message to be inactivated. Double-stranded RNA molecules may be synthesised in which one strand is identical to a specific region of the p53 mRNA transcript and introduced directly. Alternatively corresponding dsDNA can be employed, which, once presented intracellularly is converted into dsRNA. Methods for the synthesis of suitable molecule for use in RNAi and for achieving post-transcriptional gene silencing are known to those of skill in the art. p53-specific siRNA molecules suitable for use according to embodiments of the invention can be readily designed and generated by those skilled in the art based on known p53 nucleotide sequences and using well known techniques. Suitable p53-specific siRNA molecules are also available commercially, for example from Santa Cruz Biotechnology, Inc.

A further means of inhibiting p53 gene expression may be achieved by introducing catalytic antisense nucleic acid constructs, such as ribozymes, which are capable of cleaving mRNA transcripts and thereby preventing the production of wildtype protein. Ribozymes are targeted to and anneal with a particular sequence by virtue of two regions of sequence complementarity to the target flanking the ribozyme catalytic site. After binding the ribozyme cleaves the target in a site-specific manner. The design and testing of ribozymes which specifically recognise and cleave p53 sequences can be achieved by techniques well known to those in the art (for example Lieber and Strauss, 1995, *Molecular and Cellular Biology,* 15:540-551, the disclosure of which is incorporated herein by reference).

Any other inhibitor which is suitable for achieving temporary inhibition of p53 or a p53-associated pathway is also included within the scope of the present invention. Additionally, it will be readily appreciated by those skilled in the art that the combination of more than one means of direct and/or indirect inhibition of p53 or its actions, or of a p53-associated pathway may provide the most benefit.

Trophic Factors

Embodiments of the present invention provide for the use and administration of growth-promoting agents. Typically these grown-promoting agents are trophic factors.

Trophic factors suitable for use in the methods and compositions of the invention may be any trophic factors able to exert an effect on gametes or the pre- or post-implantation embryo. The trophic factors may be protein-based, polypeptide, peptide or lipid-based or any combination thereof.

The trophic factors may be natural compounds extracted from a suitable source, be synthetic or semi-synthetic compounds of the same structure and function, or synthetic analogues or mimetics of a natural trophic factor. In specific embodiments, the trophic factor may be one or more of the following: PAF, IGF-I, IGF-II, TGF-α, EGF, LIF, CSF-I or GM-CSF, or an analogue or derivative of one or more of the preceding factors. In a particular embodiment, the growth-promoting trophic factor is PAF or an analogue or derivative thereof, for example a C2-carbamyl-derivative of PAF. In another specific embodiment, the growth-promoting trophic factor is IGF-II or an analogue or derivative thereof.

Those skilled in the art will readily appreciate that for any given trophic factor the exact concentration to be used in any given circumstance should be determined empirically and will depend on a number of factors including, for example, the trophic factor to be administered, the mode of administration, the subject of the treatment (i.e. embryo, isolated cells, an individual) and the species to be treated. One skilled in the art would be able to determine, by routine experimentation, the appropriate concentration to be used in any given circumstance. By way of example only, the trophic factor may be PAF. PAF may be administered in a concentration of between about 0.01 nM and about 50 nM, between about 0.1 nM and about 20 nM, between about 0.5 nM and about 15 nM, between about 1 nM and about 10 nM, or between about 2 nM and about 10 nM.

The present invention also contemplates the provision of trophic support by artificial stimulation of the down-stream signaling pathways of trophic factors. For example in the case of PAF, transient increases in intracellular calcium concentration may be stimulated by the transient exposure of embryos to a calcium ionophore such as ionomycin. For example exposure may be for approximately 30 seconds, at a ionomycin concentration of between about 0.1 to 1 μM. Additionally, as a number of trophic factors act via a phosphotidylinositol-3-kinase (PI3K) dependent pathway (Lu et al. (2004) *Journal of Cell Science* 15, 1567-1576), this pathway may be activated in embodiments of the invention as a means of stimulating a trophic factor signaling pathway.

Administration of Agent(s)

In embodiments of the present invention as they pertain to embryos produced by ART in vitro-cultured embryos are treated directly with at least one inhibitor of p53 or a p53-associated pathway, optionally together with at least one growth promoting agent. The inhibitors and/or agents may be added as a supplement to the growth medium in which the embryos are being cultured. However, the present invention also includes within its scope embodiments in which suitable inhibitors and agents are added at other stages. For example, oocytes recovered from a female animal undergoing ART may be treated with the agents. Similarly sperm may be so treated.

Additionally the suitable agents may be administered to a female and/or male animal directly. For example the animal may be attempting to conceive naturally or may be undergoing ART treatment, such as being treated on an IVF program. Alternatively treatment may be administered to a pregnant female.

For embodiments in which methods provide for the administration of at least one growth-promoting agent and at least one inhibitor of p53 or a p53-associated pathway, the at least one growth-promoting agent and at least one inhibitor may be administered individually or alternatively they may be components of a single composition. If administered individually, the administration may be sequential or simultaneous.

Compositions according to embodiments of the invention may be prepared according to methods which are known to those of ordinary skill in the art containing the suitable agents. Such compositions may include a pharmaceutically acceptable carrier, diluent and/or adjuvant. The carriers, diluents and adjuvants must be "acceptable" in terms of being compatible with the other ingredients of the composition, and not deleterious to the recipient thereof. These compositions can be administered by standard routes. In general, the compositions may be administered by the parenteral or oral route. More preferably administration is by the oral route. Alternatively, administration may be topical or vaginal, for example in the form of an ointment, cream, lotion or gel or by way of insertion of a vaginal pessary.

It will be understood that the specific dose level for any particular individual will depend upon a variety of factors including, for example, the activity of the specific agents employed, the age, body weight, general health, diet, the time of administration, rate of excretion, and combination with any other treatment or therapy. Single or multiple administrations of the agents or compositions can be carried out with dose levels and pattern being selected by the treating physician. Regardless, the agents or compositions used in the present invention should provide a quantity of the agent sufficient to enhance embryo viability.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for parenteral administration, or in the form of a formulation suitable for oral ingestion (such as capsules, tablets, caplets, elixirs, for example).

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Formulations suitable for topical or vaginal administration comprise active ingredients together with one or more acceptable carriers, and optionally any other therapeutic ingredients, Formulations suitable for topical or vaginal administration include liquid or semi-liquid preparations suitable for penetration through the skin to the site of where treatment is required, such as lotions, creams, ointments, pastes or gels.

Creams, ointments or pastes according to the present invention are semi-solid formulations of the active ingredient for external application or for intra-vaginal application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols. The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

Gels are particularly suitable for vaginal administration. Gel compositions may be designed by means known to those skilled in the art to provide prolonged contact and promote controlled and sustained release of the active agent while minimising leakage.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which are incorporated herein by reference.

Also included within the scope of agents used in the present invention are prodrugs. Typically, prodrugs will be functional derivatives of the agents of the present invention which are readily converted in vivo to the required agents of the present invention as described herein. Typical procedures for the selection and preparation of prodrugs are known to those of skill in the art and are described, for instance, in H. Bundgaard (Ed), *Design of Prodrugs*, Elsevier, 1985, the disclosure of which is incorporated herein by reference.

In Vitro Culture Media

The present invention provides compositions for use as culture media in which the culture medium includes an effective amount of at least one inhibitor of p53 or a p53-associated pathway, optionally also including at least one growth-promoting agent, in addition to the necessary nutrients and co-factors required for in vitro growth and development of gametes or embryos.

For in vitro incubation and culture of gametes or embryos during ART procedures, a range of suitable media are available, the types and compositions of which are well known to those of skill in the art. Preferably the culture medium contains at least water, salts, nutrients, essential amino acids, vitamins and hormones, and may also include one or more growth factors. A variety of suitable culture media is commercially available, for example Earle's media, Ham's F10 media and human tubal fluid (HTF) media.

The present invention also contemplates the co-culture in vitro of embryos on a layer of 'feeder cells' by methods known to the art. Appropriate 'feeder cells' for co-culture may include, for example, bovine oviductal cells or human tubal epithelial cells.

Loss-of-Function Mutations

The present inventor's results show that ART causes up-regulation of p53 and that this is a major cause of the embryopathy induced by ART. p53 causes the synthesis of a number of effectors and regulatory elements of apoptosis, including the Bax protein, leading to the activation of caspases and consequent cell death. Thus, the presence of loss-of-function (LOF) mutations in p53 or components of p53-associated pathways may favor the survival of ART embryos.

Thus ART may provide a positive selection pressure for loss-of-function (LOF) mutations in the p53 gene, or genes encoding components of p53-associated pathways, even in the hemizygous state. Selection that favours LOF mutations may result in an over-representation of tumour susceptibility in offspring produced by ART. Although the germ-line frequency for such LOF mutations is low, selection pressure of the scale observed in the mouse model could result in marked shifts in gene frequency over time. Applied to human ART practice, the accumulation of LOF mutations will have profound implications for the use of the technology.

Accordingly, the present invention provides methods of protecting embryos, in particular embryos produced by assisted reproductive technologies, from positive selection pressures for inherited, or acquired, defects or from the accumulation of LOF mutations in the p53 gene or genes encoding components of p53-associated pathways.

The present invention will now be further described in greater detail by reference to the following specific examples, which should not be construed as in any way limiting the scope of the invention.

EXAMPLES

General Methods

Mice: p53 knockout mice are from the B6.129S2-Trp53$^{tm1Tyj}$ strain (p53−/−) backcrossed with C57BL/6J. The mutant strain was developed in the laboratory of Dr. Tyler Jacks at the Center for Cancer Research at the Massachusetts Institute of Technology and is now bred, under licence, at the Gore Hill Research Laboratory, Royal North Shore Hospital. The strain is maintained by mating heterozygous females to homozygous males, and specific matings are set up to produce p53−/−, p53+/− and p53+/+ mice as required. Tail tissue is collected from all weanlings and genotyped by PCR using the following primers 5'-CTT ggg Tgg AgA ggC TAT TC-3' & 5'-Agg TgA gAT gAC Agg AgA TC-3' for the knock-out allele and 5'-ATA ggT Cgg Cgg TTC AT-3' & 5'-CCC gAg TAT CTg gAA gAC Ag-3' for the wild type allele.

Mouse IVF: Females superovulated by 5 IU pregnant mare serum gonadotrophin followed 48 h later by 5 IU human chorionic gonadotrophin. Oocytes were collected 13-15 h after hCG and washed. Epididymal sperm collected from the epididymides of male mice (14-35 weeks old) of proven fertility is immediately placed into 1 ml of medium. Sperm were allowed to disperse for 10 min at 37° C. and were then added to the oocytes at $0.1 \times 10^6$/ml. Fertilisation was performed in a final volume of 1 ml of medium. Oocytes and sperm were cultured together for 5 h at 37° C. in 5% $CO_2$ in air. The oocytes were then retrieved, washed in Hepes-buffered HTF and their fertilisation status assessed by microscopic detection of pronuclei and polar bodies. Fertilised oocytes were transferred to drops of modified HTF medium under mineral oil and their development status assessed each 24 h.

Example 1 p53 Expression in Mouse Embryos

Example 1(A)

mRNA Expression

RT-PCR was used to compare the expression of p53 mRNA in fresh p53+/+ mouse embryos (embryos fertilised and grown in the reproductive tract) and IVF mouse embryos. For IVF embryos, the model uses a graded range of stress induced by IVF and culture under conditions of increasing growth factor deprivation. Primers were designed (5'-GGA GTC TTC CAG TGT GAT GAT, 3'-GGG ACA GCC MG TCT GTT ATG) that successfully produced an RT-PCR product of the correct size (429 bp) and sequence (SUPAMAC) for the p53 gene. Groups of 5 embryos, oocytes or sperm were pooled. mRNA was extracted and RT-PCR performed.

p53 product was detected in oocytes, zygotes, 8-cell, morulae and blastocyst stage mouse embryos collected from the reproductive tract but not in epididymal sperm. In 2-cell embryos detection was variable. Incubation of zygotes in the transcription inhibitor α-amanitin had no effect on qualitative expression of p53 RNA in zygotes, but incubation of 2-cell embryos in α-amanitin gave embryos that were p53 mRNA negative after 24 h (normally the 8-cell stage). This result indicates that p53 mRNA in the zygote and early embryo was a product of the gametes (probably mainly oocytes) but that its continual expression past the 2-cell stage required new transcription from the zygotic genome. Quantitative RT-PCR of p53 was performed to compare expression of p53 mRNA in fresh and IVF embryos. Equivalent levels of RNA were found in the oocyte, zygote, morulae and blastocyst of fresh embryos; the levels were 50-70% lower in late 2-cell embryos than in other development stages (data not shown). A similar pattern of mRNA expression was observed in fresh and IVF embryos.

Example 1(B)

Protein Expression

F1 (C57BL/6j×CBA/J), C57Bl6j and p53−/− embryos or sperm were used to examine p53 protein expression levels. T47D breast cell line was used as a positive control for the detection of p53. Four to eight week old females were superovulated by i.p. injection of 10 IU pregnant mare serum gonadotrophin (Folligon, Intervet International, Boxmeer, The Netherlands) followed 48 h later by 10 IU human chorionic gonadotrophin (hCG, Chorulon, Intervet). Females were either left unmated or paired with males of proven fertility. Day 1 of pregnancy was confirmed by the presence of a copulation plug the following morning.

Sample Collection

Mice were killed by cervical dislocation. Cumulus masses or embryos were flushed from the reproductive tract with Hepes-buffered human tubal fluid medium with 3 mg BSA/ml (Hepes-HTF-101.6 mM NaCl, 4.69 mM KCl, 0.2 mM $MgSO_4$, 0.37 mM $KH_2PO_4$, 21.4 mM Na lactate, 2.78 mM glucose, 2.04 mM $CaCl_2$, 5 mM $NaHCO_3$, 0.33 mM Na pyruvate and 21 mM Hepes pH 7.4). All components of the medium were tissue culture grade from Sigma (St. Louis, Mo.) and contained 3 mg BSA Fraction V/ml unless otherwise stated (CSL Ltd, Melbourne, Vic, Australia). Zygotes were collected 20-21 h after hCG and freed from their cumulus cells by brief exposure to 300 IU hyaluronidase (Sigma) in Hepes-HTF. Fresh 2-cell embryos, morulae and blastocysts were collected from the reproductive tract at 48 h, 72 h and 96 h, respectively.

Mouse sperm was collected from the epididymides of male mice (10-15 weeks old) of proven fertility and immediately placed into 1 ml of medium (HTF media). Sperm were allowed to disperse for 10 min at 37° C. Sperm concentration and motility was assessed by haemocytometer and the sperm suspension diluted to $0.5 \times 10^6$/ml in HTF media containing 3 mg/ml albumin. The sperm was incubated for 1, 2, 3 or 4 hours and then collected by centrifugation.

Western Blot Analysis

Embryos or sperm were collected and washed 3 times in cold PBS and transferred in a maximum volume of 1.5 µl PBS into 1.5 µl of 2× extraction buffer (2×PBS, 2% Triton X-100, 24 mM deoxycholic acid, 0.2% sodium dodecyl sulfate, 20 mM NaF, 20 mM $Na_4P_2O_7$, 2 mM PMSF, 3.08 µM aprotinin, 42 µM leupeptin and 2.91 µM pepstatin A—all from Sigma). Cells were lysed by three cycles of freezing in liquid nitrogen and thawing (with vortexing). Protein samples were diluted with 1 µl of 5× Laemmli buffer (50 mM Tris-HCl, 5 mM EDTA pH 8.0, 12.5% Sodium dodecyl sulfate, 0.05% bromophenol blue and 25% beta-mercaptoethanol), incubated 10 min at 60° C. and run on 20% homogenous SDS polyacrylamide gels (Pharmacia; Sweden) using PhastSystem apparatus separation and control unit (Pharmacia). Proteins were blotted into PVDF membranes (Hybond-P, Amersham Pharmacia) in a semi-dry blotting apparatus overnight using transfer buffer (12 mM Tris PH 7.0, 96 mM Glycine and 20% methanol). Nonspecific binding was blocked by 5% skim milk in PBS supplemented with 0.05% Tween-20 (PBST) at room temperature for 1 h. Membranes were probed with or 1:5000 diluted monoclonal anti-LIS-1 antibody overnight at 4° C. in 2.5% skim milk, and detected with horse radish peroxidase (Jackson ImmunoResearch Laboratories, West Grove, Pa., USA) conjugated secondary antibody. Membranes were developed with Femto SuperSignal Chemiluminescent Substrate (Pierce, Rockford, Ill., USA) for 5 min at room temperature.

FIG. 1A clearly illustrates that the expression of p53 increases with time as sperm are incubated capacitation media. Similarly, FIG. 1B demonstrates that p53 expression in the embryo increases with development of the embryo, at least from a 1-cell embryo through to blastocyst. Further, p53 expression is higher in embryos cultured in vitro than in embryos collected fresh from the reproductive tract.

FIGS. 1C and 1D confirm the specificity of the assays. In blastocysts from p53−/− embryos no p53 expression was detected whereas p53 protein was readily detected in blastocysts from p53+/+ embryos (FIG. 1C). Further, FIG. 1D confirms that the increased p53 expression observed following in vitro culture was not a consequence of an overall change in the pattern of protein expression in the embryos, as evidenced by the maintenance of expression of the constitutively expressed protein LIS-1.

Example 2

Immunolocalisation of p53 in Mouse Embryos

The expression pattern of p53 protein in pre-implantation mouse embryos was investigated using immunofluorescence. Embryos were washed 3-times (washing media: PBS with 0.1% BSA, 0.1% Tween-20) and fixed with fresh 2% paraformaldehyde (Sigma) in PBS PH 7.4 for 1 h at room temperature. Embryos were permeabilised for 30 min at room temperature in PBS with 2% BSA, 0.2% Tween-20 and 0.2% Triton X-100 and blocked in 2% BSA and 30% blocking serum for 1-3 h. p53 antigen was stained overnight at 4° C. with 2 µg anti-p53 sheep polyclonal antibody/ml (Oncogene Research Products (PC35) or rabbit polyclonal anti-Bax (Santa-Cruz Biotechnology, N-20) in PBS with 2% BSA and then 5 µg rabbit anti-sheep FITC conjugated antibody/ml for 1 h at room temperature (green channel). Controls were 2 µg non-immune IgG/ml instead of primary antibody. Immunofluorescence images were observed using a BioRad Radiance confocal microscope (Australian Key Centre for Microscopy and Microanalysis, University of Sydney) using a Nikon Plan Apo 60X/1.40 oil immersion objective. Images were captured using LaserSharp 2000 Version 4.0 (build 365) software. Microscope and laser settings were adjusted such that no fluorescence was observed with non-immune control. All test specimens were observed with these settings and settings the same. Quantitative analysis of staining was performed using NIH Image software. For imaging the whole embryo 1 µM sections were performed using the z-sectioning facility of the microscope.

Figure 2:
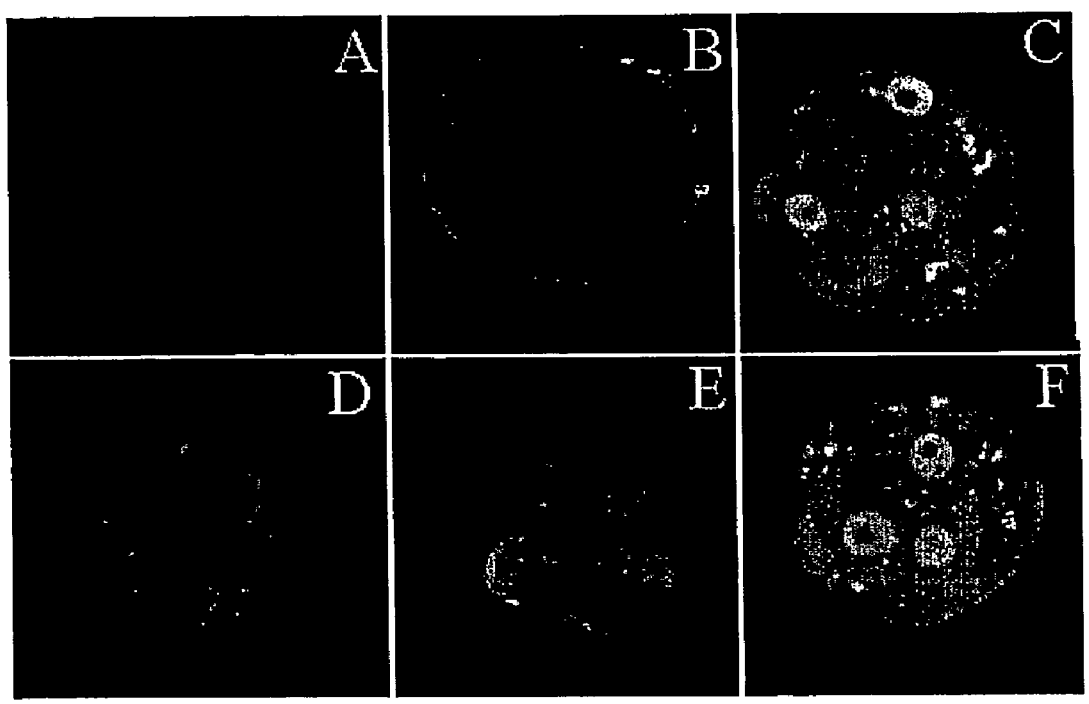
FIG. 2. Immunolocalisation of p53 in p53+/+ mouse blastocysts (A-C) and morulae (D-F) for embryos collected fresh from the reproductive tract (A&D), those fertilised in the reproductive tract but then cultured in vitro (B & E) and those produced by in vitro fertilisation and then cultured in vitro (C & F). Embryos were cultured individually in 10 μL of media. Images were single confocal sections through each image. Staining, imaging, laser settings and image capture was performed under identical conditions for all embryos.

The expression of immunodetectable p53 protein (FIG. 2) was low in preimplantation mouse embryos collected fresh from the reproductive tract (fresh embryos) (FIGS. 2A and 2D). Embryos produced by IVF and cultured individually in 10 µl of media (FIGS. 2C and 2F) or those fertilised in the reproductive tract and then cultured in vitro in groups of 10 in 10 µl of media (FIGS. 2B and 2E) showed different patterns of p53 expression. There was little immunodetectable p53 at the morula through blastocyst stage in fresh embryos and no evidence of accumulation of protein within the nucleus of the embryos cells. In contrast, there was a substantial accumulation of p53 in IVF embryos with intense nuclear localisation. There was only modest difference in p53 prior to the 8-cell stage, but greatly increased expression at each stage thereafter. By the 8-cell stage onwards, many IVF embryos showed nuclear staining as the predominant pattern of staining with relatively less cytoplasmic staining. This pattern of protein expression correlates with the pattern of embryopathy after ART, with most embryo loss occurring after the 8-cell stage.

The regulation of protein expression (Example 1B and 2), but not mRNA levels (Example 1A), suggests that the regulation of p53 is at the post-transcriptional level.

Example 3

Viability of Embryos with p53 Loss-of-Function Mutations

The correlation between high levels of p53 expression and poor embryo viability following ART (Examples 1B and 2) argues that p53 is a major effector of the responses of the embryo to cell stress. As disclosed herein, this hypothesis is confirmed by observations of improved viability of embryos with loss-of-function (LOF) mutations to p53. Mating of p53+/−×p53+/− or p53+/+×p53+/+ parents was performed by IVF and the resulting zygotes cultured for 96 h. A greater proportion of embryos from the p53+/−×p53+/− cross reached the blastocyst stage (75% v 57%) and embryos had more cells (P<0.01) and fewer apoptotic cells (P<0.001) compared to embryos resulting from wild-type crosses. The p53+/−×p53+/− cross also resulted in a reduction in the number of embryos that were markedly retarded in development or showed a degenerating of fragmented morphology (5% v 19%) and 3 times as many p53−/− embryos were hatched from their zona pellucida after 96 h culture (36%) than was the case for p53+/+ embryos (11%).

Morphologically normal blastocysts were selected for transfer after zygotes from p53+/−xp53+/− crosses were cultured in vitro for 96 h. There was a significantly higher pregnancy rate and higher proportion of viable foetuses than for embryos from p53+/+xp53+/+ crosses. A foetal viability rate of 4.7%; 9.9%; and 60.0% per embryo transferred was observed for +/+; +/− and −/− genotypes, respectively. This highly significant skewing of the genotype was not a normal feature of the mouse strain since natural mating of the same parental lines resulted in normal Mendelian segregation at birth. When +/+ embryos were collected fresh from the reproductive tract and were transferred immediately to pseudopregnant foster mothers, the foetal viability rate was 57%. Thus the absence of the p53 gene seemed to compensate for the adverse effects of ART and consequently resulted in an increased foetal viability rate.

Example 4

Inhibition of p53 and Embryo Viability p53 has numerous important cellular functions and as a consequence its permanent inhibition as a means of improving embryo viability is undesirable. The results described above indicate that the normal expression of p53 in the embryo within the reproductive tract is very low and thus it can be anticipated that providing the inhibition is short-term there would not be adverse effects and may improve embryo viability.

This hypothesis was tested using two different types of p53 inhibitor, a small molecule inhibitor (Example 4A) and a nucleic-acid based inhibitor, being a p53-specific siRNA molecule (Example 4B).

Example 4(A)

Small Molecule Inhibitor

A recently developed selective inhibitor of p53, pifithrin-α (PFTα [2-(2-imino-4,5,6,7-tetrahydrobenzothiazol-3-yl)-1-p-tolylethanone], Sigma-Aldrich), is a small molecule that reversibly blocks p53-dependent transcriptional activation and apoptosis (Komarov et al., 1999, *Science* 285, 1733-1737). PFT-α was prepared initially by solubilising to a concentration of 10 mM in dimethylsolfoxide and diluted to working concentrations.

(i) Treatment of Embryos with PFT-α

Figure 3:
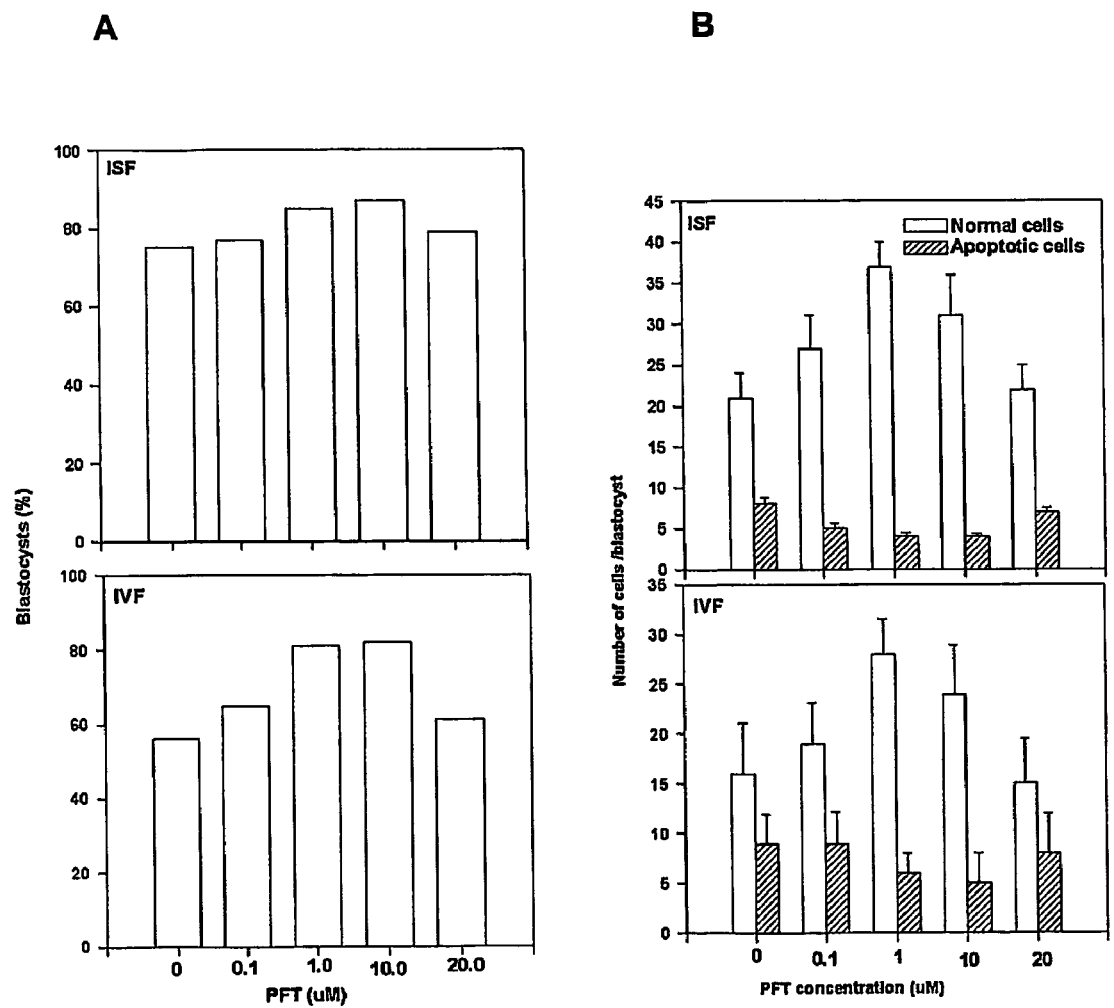
FIG. 3. The effect of short term inhibition of p53 in embryos by PFT-α on (A) the proportion of embryos developing to the blastocyst stage and (B) the number of cells per blastocyst. Pifithrin-α (PFT-α) was added as a media supplement to zygotes produced by either in situ fertilisation (ISF) or in vitro fertilisation (IVF).

Zygotes were produced by either fertilization in vitro (IVF) or fertilisation in situ (ISF) and cultured for 96 hours in modified HTFM medium individually in 101 μL drops. PFT-α was added as a media supplement over the dose range 0.1-20 M. The proportion of embryos developing to the blastocyst stage (FIG. 3A), the number of cells per normal blastocyst and the proportion of cells undergoing apoptosis (FIG. 3B), were assessed.

The results show that PFT-α caused a significant quadratic effect on the proportion of IVF embryos that developed to the blastocysts stage and for both ISF and IVF there was a significant improvement in the number of cells per normal blastocyst and a significant decrease in the number of cells that were undergoing apoptosis. This marked improved survival of embryos and cells is clinically relevant.

(ii) Treatment of Gametes with PFT-α

Preparation of sperm in vitro for fertilisation leads to an increase in the synthesis of p53 (see Example 1B; FIG. 1A). Furthermore production of embryos by IVF leads to a marked increase in the synthesis of p53 in resulting embryos (Example 1B; FIG. 1B). The present experiment was designed to determine if treatment of sperm and oocytes during the process of fertilisation in vitro resulted in an improvement to their fertilisation rate and the subsequent development of resulting embryos.

PFT-α preparation, IVF and embryo culture was as previously described. The study used F1 (C57Bl6j×CBAj) males and females. PFT-α was added to sperm during its capacitation and during the process of fertilisation in vitro.

4-5 h after the addition of sperm to oocytes, the oocytes were washed free of sperm and PFT-α. They were examined for the presence of 2 pronuclei as evidence of successful fertilisation. Successfully fertilised oocytes were placed in culture in 10 μL of modified HTF media, 1 zygote per 10 μL drop. They were culture for 120 h and the proportion forming morphologically normal blastocysts were recorded. The blastocysts were fixed in 2% formaldehyde and stained with 5 μG Hoechst stain/ml. The stain labels nuclei and was used to perform cell counts on each blastocyst.

Figure 4:
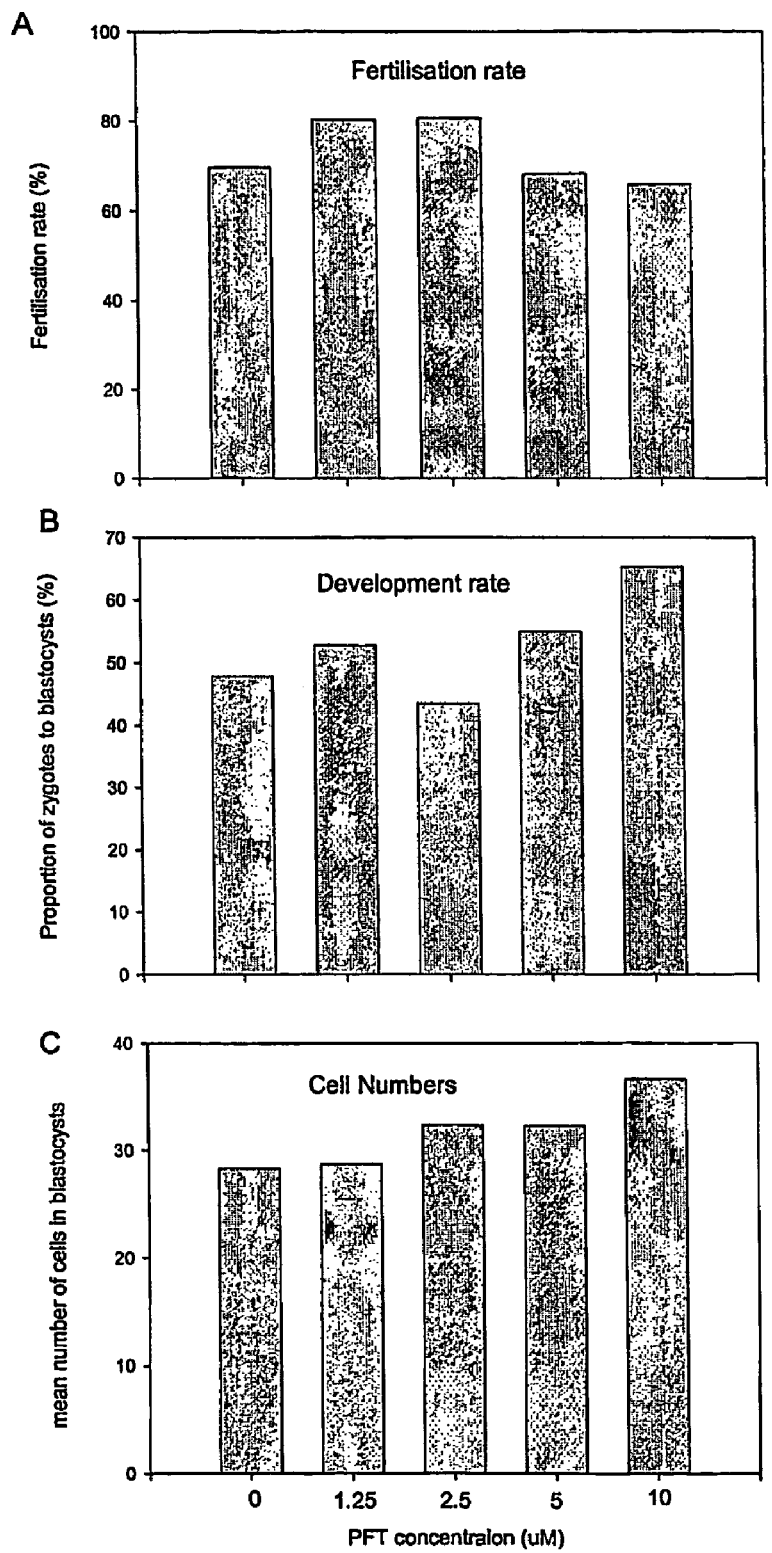
FIG. 4. The effect of short term inhibition of p53 in gametes by PFT-α on (A) the proportion of oocytes fertilized, (B) the proportion of embryos developing to the blastocyst stage and (C) the number of cells per blastocyst.

The effect of dose of PFT-A on the proportion of oocytes fertilised, the proportion of zygotes that developed to morphological blastocyst and the number of cells in each blastocysts were recorded and are shown in FIGS. 4A, B and C respectively. The effect of PFT-A dose was assessed using the SPSS statistical package. The fertilisation rate and development rate were assessed using binary logistic regression analysis while cell numbers were assessed by univariate analysis using the general linear model.

FIG. 4A illustrates that there is a dose-dependent increase in fertilisation rate in the presence of PFT-α ($P<0.01$). Of the oocytes that fertilised, there was a further dose-dependent increase in the proportion of zygotes that developed to the blastocyst stage (FIG. 4B) ($P<0.05$). Of embryos developing to the blastocyst stage there was a dose-dependent significant increase in the mean number of cells present in each embryo ($P<0.05$, FIG. 4C).

The results demonstrate that treatments that decrease the expression of p53 in gametes prior to and during fertilisation result in an improvement in fertilisation, and subsequent embryo development.

Example 4(B)

siRNA Inhibition

As an alternative to temporary inhibition of p53 using a small molecule inhibitor, the ability of transient treatment of embryos with p53-specific siRNA to inhibit p53 expression was investigated. Oligonucleotides designed as siRNA against mouse p53 or control nonsense siRNA sequences were used, both of which were obtained from Santa Cruz Biotechnology, Inc. The siRNA oligonucleotides were prepared as 90 nM with siMHTF media (102 mM NaCl, 4.6 mM KCl, 0.20 mM $MgSO_4$, 0.4 mM $KH_2PO_4$, 21.4 mM Na lactate, 1 mM glutamine, 0.33 mM Na pyruvate, 2.78 mM glucose, 2.0 mM $CaCl_2$, 25 mM $NaHCO_3$, pH 7.35; 285 mOsm/l) containing 3 mg polyvinyl-pyrrolidone/ml (PVP) (Sigma). All media were sterilized with a 0.1 μm filter. Cells were transfected with the siRNA molecules in the presence of 25% (v/v) oligofectamine (Invitrogen). Oligofectamine was prepared in siMHTF, mixed gently and incubated for 5-10 minutes at room temperature. 17 μl of siRNA was added to 3 μl of 25% oligofectamine, mixed gently and incubated for 15-20 minutes at room temperature. It was then brought to 100 µL with siMHTF, giving a final oligonucleotide concentration of 15 nM.

Embryos were collected from F1 (C57BL6×CBA/j) mice. Females were super ovulated with PMSG and HCG (5 I.U.). Zygotes were collected ~10 h after mating and cultured for 96 h in modHTF media plus penicillin and phenol red, pH 7.35; 285 mOsm/l) at 37° C. in 5% $CO_2$.

Embryos were incubated with either p53 siRNA or control siRNA for 4 h at 37° C. in 5% $CO_2$. Embryos were then thoroughly washed and placed in conventional culture and the development and expression of p53 in resulting embryos analyzed.

Staining for p53 was performed by washing embryos three-times (washing media: PBS with 0.1% BSA, 0.1% Tween-20 and 0.2% sodium azide) and fixing with fresh 2% formaldehyde (Sigma) in PBS PH 7.4 for 1 h at room temperature. Embryos were permeabilized for 30 min at room temperature in PBS with 2% BSA, 0.3% Tween-20 in the presence of 2% formaldehyde and after washing blocked in 2% BSA and 30% goat serum (Sigma) for 1-3 h. p53 antigen was stained overnight at 4° C. with freshly prepared 1:50 sheep polyclonal antihuman p53 antibody (Oncogene Research Products) in PBS with 2% BSA and then anti-sheep FITC conjugated antibody (Sigma) for 1 h at room temperature. Staining was on a Nikon epifluorescence microscope.

Figure 5:
FIG. 5. Staining of blastocysts with anti-p53 antibody after treatment with either p53-specific siRNA (A) or non-specific scrambled (control) siRNA (B).
Figure 5:
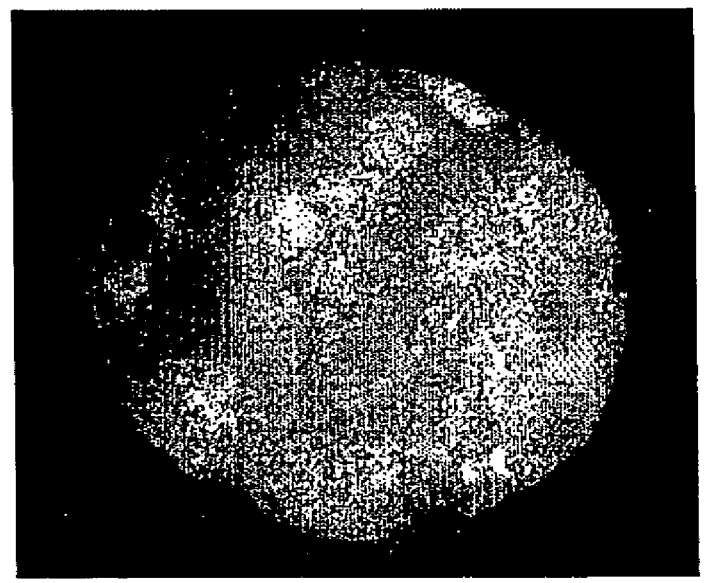

FIG. 5 shows that even a single application of p53 siRNA to developing embryos caused marked down-regulation of p53 expression and a loss of p53 staining from the nucleus, its primary site of action.

After treatment of zygotes with p53 siRNA or control siRNA for 4 h followed by culture in vitro under standard conditions less p53 staining was observed in the resulting blastocysts. Further, the blastocysts resulting from treatment with p53 siRNA had significantly more cells per embryos— an average increase of 12.5% ($P<0.05$) (data not shown). Use of oligofectamine or control siRNA had no adverse effect on embryo development to the blastocyst stage.

These results indicate that inhibition of p53 expression activity by means other than PFT-α or genetic deletion also has the capacity to improve embryo development.

Example 5

Treatment of Bovine Sperm with PFT-α on Embryo Viability

Example 4 demonstrates the beneficial effect of temporary inhibition of p53 on mouse embryo viability. As described below, experiments were then conducted to investigate the effect of treatment of bovine sperm with PFT-α on bovine embryo viability.

All embryo manipulations were performed at 39° C. except for oocyte harvesting and activation which was performed at room temperature. All procedures were performed in 4-well Nunc dishes in Tissue Culture Medium 199 (TCM-199) supplemented with HEPES (TCM-H TCM-199; Gibco™ BRL/Life Technologies, Melbourne, Victoria, Australia) without mineral oil overlay, unless otherwise indicated.

Bovine ovaries collected from 2 different local slaughterhouse, transported at 30-35° C. to the laboratory and washed on 39° C. physiologic saline (0.9% NaCl; Baxter Healthcare Pty., Ltd., NSW, Australia). Ovarian antral follicles (2-8 mm) were aspirated using an 18-gauge needle and collected into TCM-H with 30 IU $ml^{-1}$ heparin (Pharmacia & Upjohn Pty., Ltd., Perth, Wash., Australia) and 2% gamma radiated fetal bovine serum (FBS; JRH Biosciences Pty., Ltd., Melbourne, Victoria, Australia). Cumulus oocyte complexes (COCs) showing an even cytoplasm and surrounded by at least three layers of compact cumulus cells were collected from the follicular fluid. COCs were incubated and matured groups of 50 in 600 µL of TCM-199 (Gibco™ BRL/Life Technologies, Melbourne, Victoria, Australia) supplemented with 5 µg $ml^{-1}$ LH (Lutropin-V®, Bioniche Animal Health, A/Asia Pty. Ltd., Armidale, Victoria, Australia), 1 µg $ml^{-1}$ β-Estradiol, 100 IU/100 µg $ml^{-1}$ penicillin/streptomycin and 10% FBS at 39° C. in 5% $CO_2$ in air for 18-22 hours without oil layer.

Frozen/thawed semen from an elite bull was placed on a Percoll gradient and centrifuged at 600×g for 20 minutes. The top layers were removed and the sperm concentration and motility of the pellet determined. Preparations of PFT-α were added to the sperm preparation at concentrations of between 0.3 and 3 µM and incubated for 1 h. Sperm was then added to COCs ($1×10^6$ sperm $ml^{-1}$) in Bovine Vitro Fert (Cook® Australia, Brisbane, QLD, Australia) medium supplemented with heparin (0.5 mg $ml^{-1}$), hypotaurine (1.65 µg $ml^{-1}$), epinephrine (0.27 µg $ml^{-1}$) and penicillamine (4.5 µg $ml^{-1}$) for 24 hours at 39° C. in 5% $CO_2$.

Following 24 hours sperm-egg co-incubation, cumulus cells were removed from presumptive zygotes by vortexing 90 seconds in a 15 ml centrifuge tube (Becton-Dickinson Labware, N.J., USA). Denuded embryos were washed in TCM-H supplemented with 5% FBS before being transferred into 4-well Nunc plates (Nunc™, Roskilde, Denmark) containing Bovine Vitro Cleave (Cook® Australia) for 5 days in 5% $O_2$; 5% $CO_2$ and 90% N2. On day 5 embryos were transferred into Bovine Vitro Blast (Cook® Australia) medium supplemented with 4% charcoal-treated bovine serum, 4% supernatant obtained from embryonic carcinoma cells containing fibroblast growth factor-4 (FGF-4) and 20 µg $ml^{-1}$ heparin.

In vitro maturation and fertilization was carried out at 2 different locations using different sources of oocytes and different operators.

Figure 6:
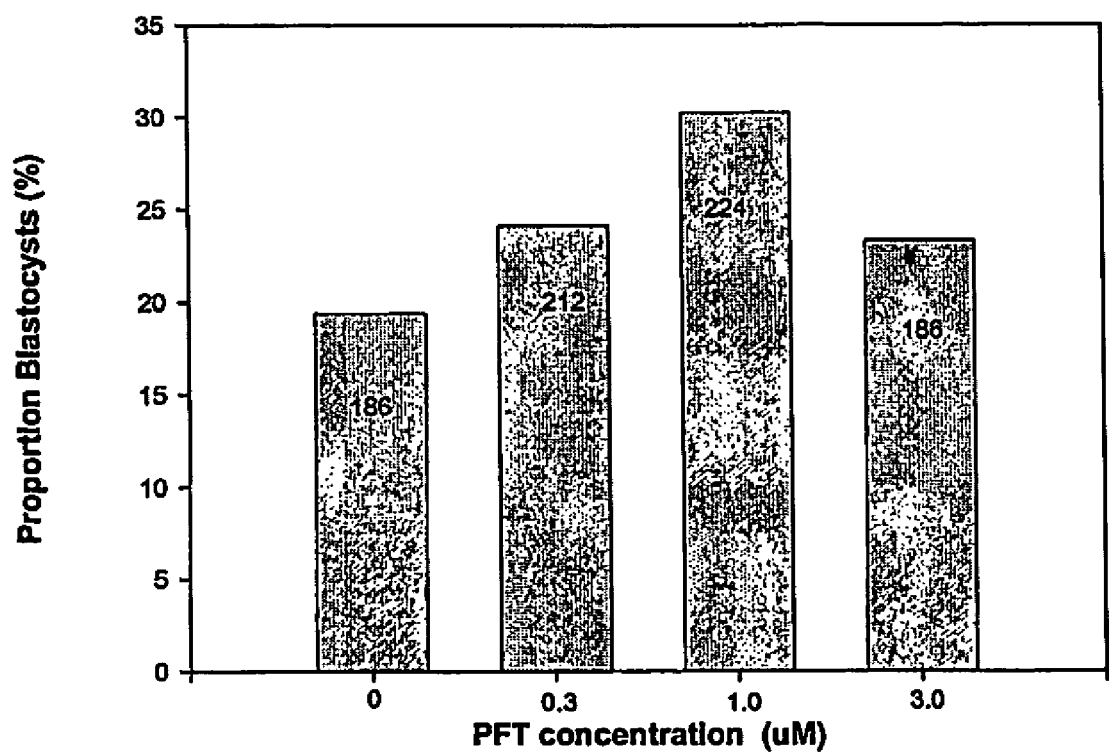
FIG. 6. Effect of treatment of bovine sperm with PFT-α for one hour prior to insemination on the subsequent proportion of oocytes forming blastocysts (the number of oocytes in each treatment is shown in each bar).

The proportion of blastocysts were determined on Day 7 (Day 0=fertilization). The results are shown in FIG. 6. The results show that, compared to the control, there was a significant positive effect of PFT-α treatment of sperm on the proportion of resulting embryos that developed to morphological blastocysts. This effect occurred independently of the location of the procedures or the operators. These results are consistent with those obtained for treatment of mouse embryos with p53 inhibitors, thereby demonstrating the broad applicability of the method and compositions of the present invention.

Example 6

ART Reduces the Capacity of Embryos to Respond to PAF

Mammalian embryos express a receptor for PAF, and activation of this receptor elicits a transient increase in the embryo's intracellular calcium concentration (Emerson et al., 2000, *Journal of Biological Chemistry* 275, 21905-21913; Lu et al., 2003, *Biology of Reproduction* 69, 106-116).

Figure 7:
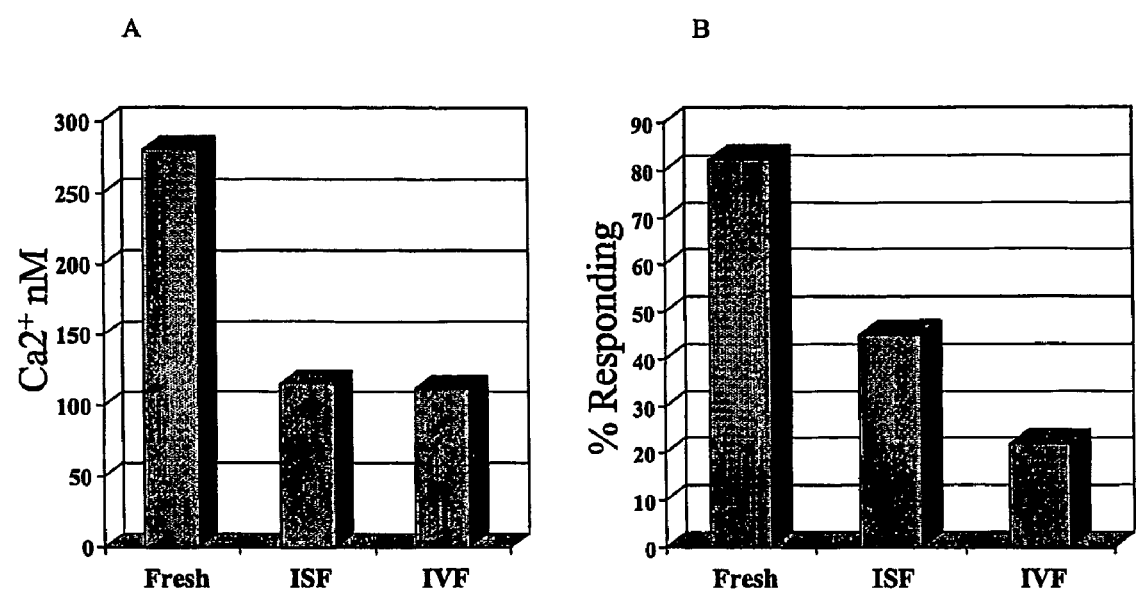
FIG. 7. The response of embryos to the addition of exogenous PAF. Embryos were either collected fresh from the reproductive tract (fresh), fertilized in the reproductive tract and cultured in vitro (ISF) or fertilized and cultured in vitro (IVF). Response was measured by the amplitude of intracellular calcium concentration (A) and the proportion of 2-cell embryos responding (B).

Mouse embryos were incubated with exogenous PAF and the intracellular $Ca^{2+}$ concentration was determined as described by Emerson et al. (2000). Embryos tested were: (i) those fertilized in the reproductive tract and collected fresh from the reproductive tract (fresh); (ii) embryos produced by IVF and cultured in vitro (IVF); and (iii) embryos fertilized in the reproductive tract and cultured in vitro (ISF). FIG. 7 illustrates that the proportion of 2-cell IVF embryos that responded to the addition of exogenous PAF is substantially reduced in comparison to fresh and ISF embryos. This reduced signaling correlated with poor development of the embryos in vitro.

Example 7

Co-Treatment of Embryos In Vitro with PAF and PFT-A

To test the hypothesis that up-regulation of p53 may be a contributor to the limited benefit achieved by provided by exogenous trophic factors, the development of mouse embryos cultured in vitro was monitored following either: (i) inhibition of p53 by the synthetic small molecule p53 inhibitor, PFT-α; (ii) exposure of embryos to exogenous PAF; or (iii) a combination of (i) and (ii). PFT-α was prepared as described above. PAF (1 hexadecyl/octadecyl-2-acetyl-sn-glyceryl-3-phosphocholine; an approximately equimolar mixture of hexadecyl and octadecyl isoforms of PAF, Sigma Chemical Company) was stored as a stock solution of 10 mg/ml in chloroform at −20° C. Aliquots were placed in sterile siliconised glass tubes and dried under $N_2$. The PAF was solubilised by the addition of modified-HTF with 3 mg BSA/ml, followed by vigorous vortexing for 3 mins and then allowed to stand for 1 hour at 37° C. with gentle mixing. Desired concentrations of PAF were then achieved by serial dilution in modified-HTF.

Females were superovulated by 5 IU pregnant mare serum gonadotrophin followed 48 h later by 5 IU human chorionic gonadotrophin. They were placed with mature males overnight. Zygotes were collected on day 1 of pregnancy at ~1300 h. Zygotes were cultured for 96 h in modified HTFM medium individually in 10 μl drops. The proportion of embryos developing to morphologically normal blastocysts, the number of cells in each blastocyst and the number of apoptotic cells per blastocyst were assessed in media containing 0, 10 nM PAF, 10 μM PFT-α, or PAF+PFT-α.

Figure 8:
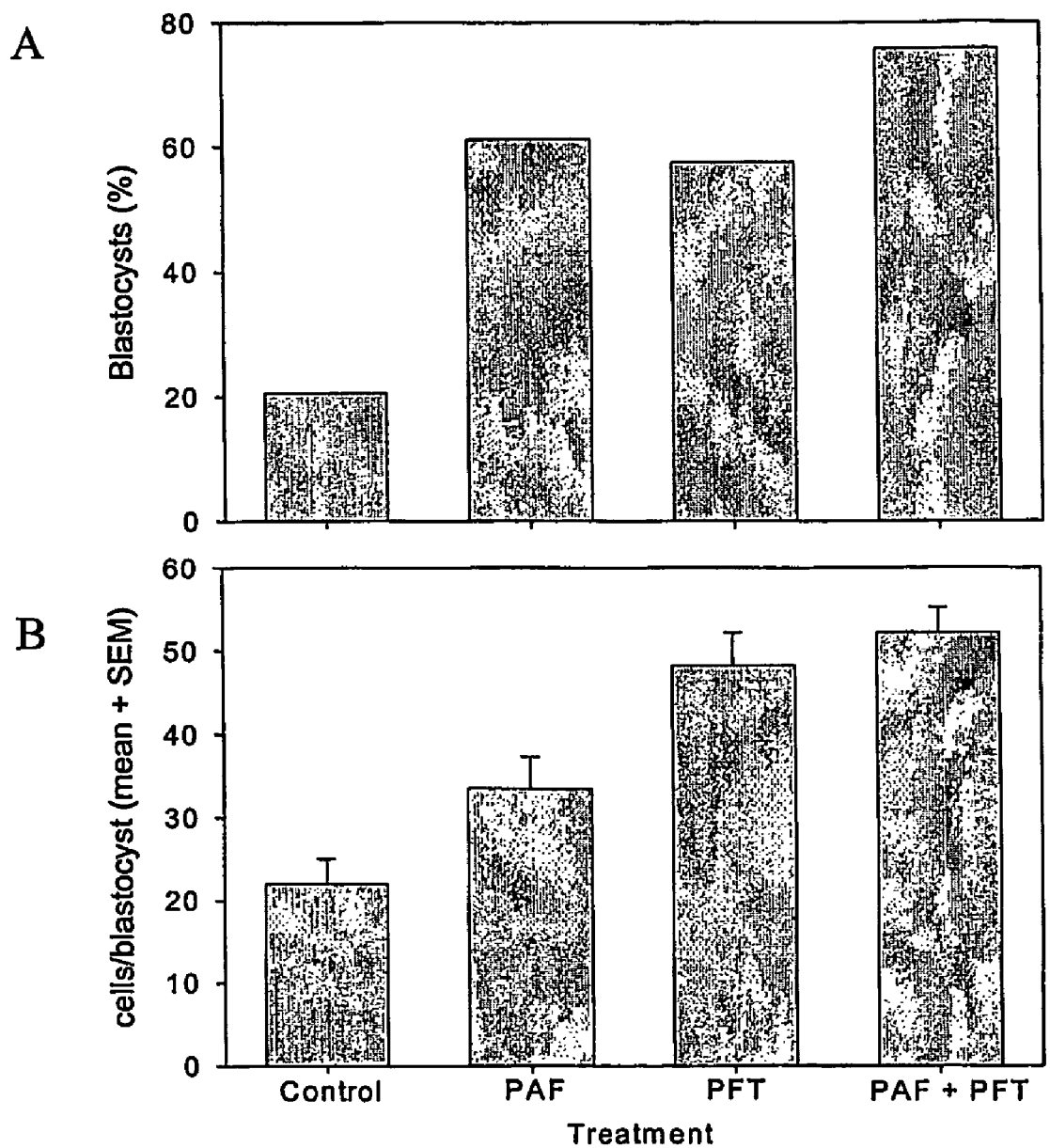
FIG. 8. The effect of co-treatment of AF and PFT-α on the development of in vitro cultured embryos as measured by the proportion of embryos progressing to blastocysts (A) and the mean number of cells per blastocyst (B). Embryos were treated with PAF alone, PFT-α alone or both PAF and PFT-α. Control embryos were cultured in the absence of PAF and PFT-α.

As FIG. 8 shows, single treatments using PFT-α and PAF both resulted in an increase in embryo viability as assessed by the proportion of embryos that successfully developed to the blastocyst stage, while the combined treatment of PFT-α and PAF caused a significant further improvement (P<0.05) in development compared to either single treatment. This effect was also observed in the number of cells present within each embryo, with the combined treatments having significantly more cells than either treatment alone (P<0.05).

Example 8

Effect of Combined Treatment of IGF-II and PFT-α on Embryo Development In Vitro

The normal development of the early embryo requires the action of autocrine and paracrine (and possibly endocrine) trophic factors. These factors act to induce the normal survival and proliferation of the embryo and reduce the incidence of cell cycle arrest and apoptosis.

One example of an autocrine trophic factor is PAF and as described in Example 6 above, the culture of embryos in vitro compromises the capacity of embryos to respond to PAF. There are many other potential trophic factors, examples of which include insulin-like growth factors-I (IGF-I) and -II (IGF-II), transforming growth factor-α (TGF-α), epidermal growth factor (EGF), leukemia inhibitory factor (LIF), colony stimulating factor-I (CSF-I), and granulocyte-macrophage colony stimulating factor (GM-CSF). The present inventor has previously shown that the expression of both IGF-I and IGF-II by the early embryo is compromised by IVF and culture (Stojanov et al., 1999, *Molecular Human Reproduction* 5: 116-124; Stojanov and O'Neil, 2001, *Biology of Reproduction* 64: 696-705). Both IGF-I and IGF-II when applied to embryo in vitro have a beneficial effects on embryo development (O'Neil, 1997, *Biology of Reproduction* 56: 229-237).

As described in Example 7, when PAF treatment is combined with PFT-α there is an additive benefit to the developing embryo. Since many trophic factors act on the embryo, the inventor investigated whether an additive benefit between trophic factors and p53 inhibition is a general principle. Accordingly, the effects of IGF-II on embryo development was analyzed with and without the simultaneous presence of PFT-α.

The IGF-II used was human recombinant insulin-like growth factor-II (expressed in *E. Coli*) (Sigma Chemical Co.), reconstituted with a minimal volume of 0.1M acetic acid and immediately diluted with modified-HTF to a concentration of 50 μg/ml. Aliquots were frozen at −70° C. Upon thawing, aliquots were serially diluted with modified-HTF.

Zygotes produced by IVF from F1 crosses were prepared and cultured as described above, with 1 embryo per 101 μl drop of media. Zygotes were cultured for 96 h in modified HTFM medium individually in 10 μl drops. The proportion of embryos developing to morphologically normal blastocysts, the number of cells in each blastocyst and the number of apoptotic cells per blastocyst were assessed in media containing 10 ng/ml IGF-II, 1 μM PFT-α, or IGF-II+PFT-α. The results are shown in Table 1.

TABLE 1

| Treatment | Control | IGF-II | PFT | IGF + PFT |
|---|---|---|---|---|
| % blastocyst | 31 | 42 | 44 | 52 |
| Cells/blastocyst | 23 ± 4 | 29 ± 2 | 32 ± 4 | 35 ± 3 |
| Significance | | 0.01 | 0.01 | 0.005 |

Example 9

The Role of p53 Genotype on Gametes and Embryo Viability

The role of p53 in gamete and embryo viability was investigated by assessing the fertility and development of gametes and embryos collected from p53+/− mice.

Embryo, gamete and embryo collection was as described in previous Examples.

Figure 9:
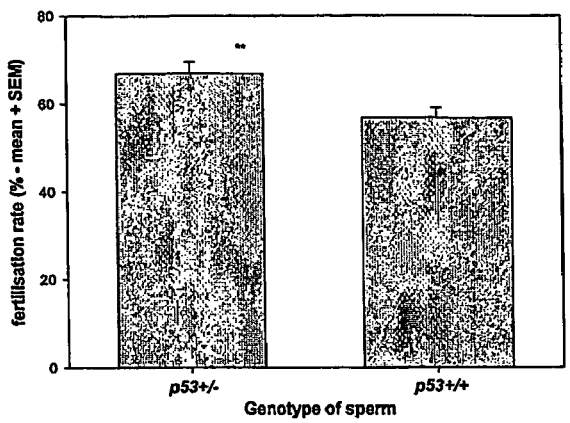
FIG. 9. The effect of p53 genotype on gamete and embryo viability. (A) The effect of sperm genotype on fertilization rate following ISF. (B) The effect of sperm genotype on the genotype of embryos resulting from IVF and ISF. (C) The effect of p53 genotype of a female animal on the number of eggs collected following superovulation.
Figure 9:
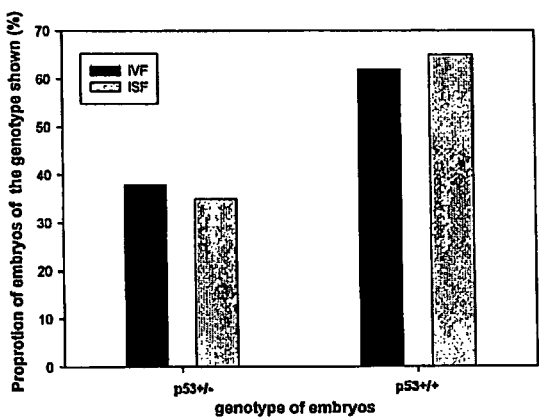
Figure 9:
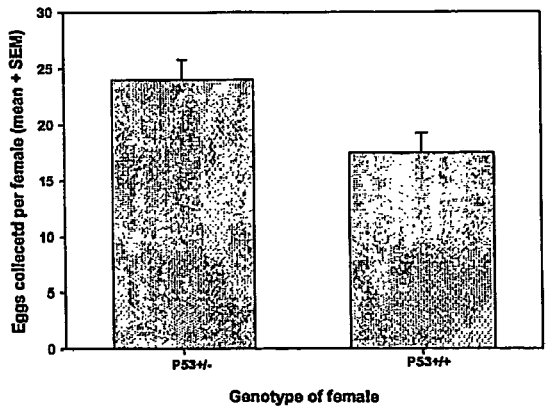

Females were mated with either wildtype (p53+/+) or heterozygous (p53+/−) males. 12 h after mating the reproductive tract was flushed and the proportion of eggs that were fertilized was assessed. The results in FIG. 9A show that there was a significantly (P<0.001) higher incidence of fertilization following mating with p53+/− males than p53+/+ males. The experiment was repeated 4 times. A similar improvement in the fertilization rate was achieved following fertilization by IVF (data not shown).

The genotype of each of the resulting zygotes was analysed to determine if the improvement in fertility rate was due to a greater fertilizing capacity by p53 null sperm. FIG. 9B shows that following fertilization by either IVF or ISF there was an unexpectedly greater proportion of p53+/+ zygotes than p53+/−, indicating that sperm produced by p53-deficient mice have a higher fertilizing capacity than sperm from wildtype animals. These results suggest that actions and agents that reduce p53 expression in males during important phases of spermatogenesis or during sperm maturation enhance the fertilizing capacity of sperm.

The effect of p53 genotype on the number of oocytes released by females after ovulation induction was also studied. FIG. 9C shows that females with only one functional p53 gene released significantly more oocytes following ovulation induction. These results suggest that actions or agents that reduce the expression of p53 in females during follicular development and ovulation improve the ovulation rate.

To assess the viability and developmental potential of embryos with different doses of the p53 gene, p53+/−× p53+/− matings were performed and embryos were either collected from the reproductive tract at the zygote stage and their development assessed over 96 h in vitro, or collected as blastocysts from the reproductive tract 4 days after mating. The development stage and morphology of each embryo was assessed and then individual embryos were genotyped by PCR. The results shown in Table 2 below demonstrate that there is a strong association between decreasing p53 gene dose and improved developmental potential for embryos collected from the zygote stage (A), but that no such association exists when embryos are collected fresh from the reproductive tract (B). These results illustrate that treatments that reduce p53 expression or activity in the early embryo will have the effect of increasing their development in vitro.

TABLE 2

Genotypes of embryos from p53+/− × p53+/− cross.
Embryos were collected as (A) zygotes on Day 1 and cultured in vitro from 96 h or (B) as blastocysts on Day 4.

| Development | Genotype result | | |
|---|---|---|---|
| Stage after 96 h (%) | +/+ | +/− | −/− |
| A | | | |
| Hatching blastocysts*** | 2 (4) | 24 (48) | 24 (48) |
| Blastocyst** | 15 (19.7) | 53 (69.7) | 8 (10.5) |
| Morulae | 14 (21.5) | 38 (58.5) | 13 (20) |
| Fragmented or degenerate*** | 20* (47.6) | 22* (52.4) | 0* (0) |
| Total* | 51* (21.9) | 137* (58.8) | 45* (19.5) |
| B | | | |
| Blastocyst | 20 (24.3) | 35 (42.7) | 27 (32.9) |

$P < 0.05$
**$P < 0.01$,
***$P < 0.001$ when compared to expected Mendelian segregation.
Prior to genotyping embryos had their zona pellucida removed to ensure that there were no adherent maternal cells or sperm present. 98% of embryos were successfully genotyped.

To assess whether the reduced p53 expression also leads to improved fetal viability of such embryos, embryos were produced by mating p53+/−×p53+/− parents. The embryos were cultured either on the day of mating (zygotes) or 3 days after mating (morulae). The embryos were collected for either 96 h or 24 h to produce blastocysts. The resulting blastocysts were transferred to the uterus of day 3 pseudopregnant females. Nine days after embryo transfer the foster mothers were examined for pregnancy and the number and genotype of the viable fetuses was assessed. The results in Table 3 below show that prolonged culture of embryos in vitro reduced their capacity to form viable fetuses, but that there was a strong negative association between the presence of the p53 gene dose and the likelihood that embryos would form viable fetuses. This association was not present when embryos were cultured for only a short period.

Thus, these results indicate that the absence of p53 expression helps protect embryos from the adverse effects of culture in vitro, suggesting that actions or agents that reduce p53 expression within embryos during their culture or manipulation in vitro have a beneficial effect on embryo development and viability.

TABLE 3

| Culture period | 96 h | | | 24 h | | |
|---|---|---|---|---|---|---|
| Implantation rate (%) | 113/195 (58) | | | 121/196 (62) | | |
| Viable fetuses | 26/195 (13) | | | 94/196 (48) | | |
| Genotype | +/+ | +/− | −/− | +/+ | +/− | −/− |
| Genotype of fetuses (% of total) | 3 (11.5) | 11 (42.3) | 12 (46.2) | 25 (26.6) | 44 (40.8) | 25 (26) |
| Assumed genotype of embryos transferred (% of total) from Table 3 | 38 (19.7) | 136 (69.7) | 20 (10.5) | 48 (24.3) | 84 (42.7) | 64 (32.9) |
| Estimated Fetal viability (%)* | 7.9 | 8.1 | 60.0 | 52.1 | 52.4 | 39.1 |

*Estimated viability is calculated by multiplying the total fetuses formed by the relative assumed frequency of the embryo genotype transferred.

Example 10

In Vitro Culture Media

In accordance with the best mode of performing the invention provided herein, a specific typical culture medium is outlined below. The following is to be construed as merely an illustrative example of a suitable medium and not as a limitation of the scope of the present invention in any way.

A suitable culture medium is modified HTF medium comprising 101.6 mM NaCl, 4.69 mM KCl, 0.2 mM $MgSO_4$, 0.37 mM $KH_2PO_4$, 21.4 mM Na lactate, 2.78 mM glucose, 2.04 mM $CaCl_2$, 25 mM $NaHCO_3$, 0.33 mM Na pyruvate, 0.11 mmol/L EDTA and 1 mmol/L glutamine, pH 7.4 supplemented with 3 mg serum albumin/ml, supplemented with 10 µM of PFT-α, and optionally 10 nM PAF.

Example 11

Compositions

In accordance with the best mode of performing the invention provided herein, specific typical compositions are outlined below. The following are to be construed as merely illustrative examples of compositions and not as a limitation of the scope of the present invention in any way.

Example 11(A)

Capsule Composition

A composition in the form of a capsule for oral administration may be prepared by filling a standard two-piece hard gelatin capsule with 50 mg of a suitable inhibitor, in powdered form, optionally including 50 mg of trophic factor, 100 mg of lactose, 35 mg of talc and 10 mg of magnesium stearate.

Example 11(B)

Injectable Parenteral Composition

A composition suitable for administration by injection may be prepared by mixing 1% by weight each of a suitable inhibitor, and optionally a suitable trophic factor, in 10% by volume propylene glycol and water. The solution is sterilised by filtration.

Example 11(C)

Composition for Parenteral Administration

A composition for intramuscular injection could be prepared to contain 1 ml sterile buffered water, and 1 mg each of a suitable inhibitor, and optionally a suitable trophic factor.

Similarly, a composition for intravenous infusion may comprise 250 ml of sterile Ringer's solution, and 5 mg each of a suitable inhibitor, and optionally a suitable trophic factor.

Example 11(D)

Topical Cream Composition

A typical composition for delivery as a topical cream is outlined below:

| | |
|---|---|
| Suitable inhibitor | 1.0 g |
| (Suitable trophic factor | 1.0 g) |
| Polawax GP 200 | 25.0 g |
| Lanolin Anhydrous | 3.0 g |
| White Beeswax | 4.5 g |
| Methyl hydroxybenzoate | 0.1 g |
| Deionised & sterilised water to | 100.0 g |

The polawax, beeswax and lanolin are heated together at 60° C., a solution of methyl hydroxybenzoate is added and homogenisation achieved using high speed stirring. The temperature is then allowed to fall to 50° C. The p53 inhibitor, and optionally trophic factor, are then added and dispersed throughout, and the composition is allowed to cool with slow speed stirring.

Example 11(E)

Gel Composition for Vaginal Administration

A typical composition for vaginal delivery as a gel includes mixing 1.0 g of a suitable inhibitor, and optionally a suitable trophic factor, together with a water-soluble bioadhesive polymer and pH buffer in purified water. To the above solution low gelling temperature agarose, is added to 100.0 g while gently stirring continuously until a uniform mixture is obtained.

The invention claimed is:

1. A method for enhancing viability of a cultured animal embryo to the blastocyst stage, the method comprising culturing the animal embryo in a medium comprising at least one p53 inhibitor, wherein the culturing enhances the likelihood that the animal embryo will develop to the blastocyst stage compared to an animal embryo cultured in a medium that does not comprise a p53 inhibitor.

2. The method of claim 1 wherein the p53 inhibitor is selected from the group consisting of: a small molecule inhibitor, a nucleic-acid based inhibitor, a peptide-based inhibitor and any combination thereof.

3. The method of claim 2 wherein the p53 inhibitor is a small molecule inhibitor.

4. The method of claim 3 wherein the small molecule inhibitor is pifithrin-α (PFT-α) or a derivative or analogue thereof.

5. The method of claim 2 wherein the p53 inhibitor is a p53-specific antisense molecule.

6. The method of claim 5 wherein the antisense molecule is a p53-specific siRNA.

7. The method of claim 1 wherein the culture medium comprises two or more p53 inhibitors.

8. The method of claim 7 wherein the two or more p53 inhibitors comprise a small molecule inhibitor and a p53-specific siRNA.

9. A method for enhancing viability of a cultured animal embryo to the blastocyst stage, the method comprising culturing the animal embryo in a medium comprising at least one p53 inhibitor and at least one growth promoting agent, wherein the culturing enhances the likelihood that the animal embryo will develop to the blastocyst stage compared to an animal embryo cultured in a medium that does not comprise a growth promoting agent and/or a p53 inhibitor.

10. The method of claim 9 wherein the growth promoting agent is a trophic factor or an analogue or derivative thereof.

11. The method of claim 10 wherein the trophic factor is selected from the group consisting of: platelet activating factor (PAF), insulin-like growth factors-I (IGF-I) and -II (IGF-II), transforming growth factor-α (TGF-α), epidermal growth factor (EGF), leukemia inhibitory factor (LIF), colony stimulating factor-I (C SF-I), and granulocyte-macrophage colony stimulating factor (GM-CSF).

12. The method of claim 11 wherein the trophic factor is PAF or an analogue or derivative thereof.

13. The method of claim 11 wherein the trophic factor is IGF-II or an analogue or derivative thereof.

14. The method of claim 9 wherein the at least one p53 inhibitor is PFT-α and the at least one growth promoting agent is PAF or an analogue or derivative thereof.

15. The method of claim 9 wherein the at least one p53 inhibitor is PFT-α and the at least one growth promoting agent is IGF-II or an analogue or derivative thereof.

16. The method of claim 9 wherein the at least one p53 inhibitor is a p53-specific siRNA and the at least one growth promoting agent is PAF or an analogue or derivative thereof.

17. The method of claim 9 wherein the at least one p53 inhibitor is a p53-specific siRNA and the at least one growth promoting agent is IGF-II or an analogue or derivative thereof.

18. The method of claim 1 wherein the embryo is fertilized in the reproductive tract of a female animal.

19. The method of claim 1 wherein the embryo is produced by assisted reproductive technology.

20. The method of claim 19 wherein the assisted reproductive technology is in vitro fertilization.

21. The method of claim 1 wherein the embryo is cryopreserved prior to culture.

22. The method of claim 1 wherein the animal is selected from the group consisting of: human, non-human primate, ovine, bovine, canine, feline, porcine, equine and murine.

23. The method of claim 22 wherein the animal is human or bovine.

\* \* \* \* \*